United States Patent
Bonutti et al.

(10) Patent No.: US 10,765,484 B2
(45) Date of Patent: *Sep. 8, 2020

(54) SYSTEMS AND METHODS FOR NAVIGATION AND VISUALIZATION

(71) Applicant: P Tech, LLC, Effingham, IL (US)

(72) Inventors: Peter M. Bonutti, Manalapan, IL (US); Justin E. Beyers, Effingham, IL (US)

(73) Assignee: P TECH, LLC, Effingham, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,666

(22) Filed: Aug. 27, 2018

(65) Prior Publication Data
US 2019/0254755 A1 Aug. 22, 2019

Related U.S. Application Data

(63) Continuation of application No. 15/299,981, filed on Oct. 21, 2016, now Pat. No. 10,058,393.
(Continued)

(51) Int. Cl.
*G06K 9/00* (2006.01)
*A61B 34/20* (2016.01)
(Continued)

(52) U.S. Cl.
CPC .............. *A61B 34/20* (2016.02); *A61B 34/30* (2016.02); *A61B 90/361* (2016.02); *A61B 90/37* (2016.02);
(Continued)

(58) Field of Classification Search
CPC ........ A61B 2090/376; A61B 2090/378; A61B 34/30; A61B 2034/105; G06T 2210/41
(Continued)

(56) References Cited

U.S. PATENT DOCUMENTS

| 319,296 A | 6/1885 | Molesworth |
| 668,878 A | 2/1901 | Jensen |
| (Continued) | | |

FOREIGN PATENT DOCUMENTS

| CA | 2641580 | 8/2007 |
| CA | 2660827 | 9/2008 |
| (Continued) | | |

OTHER PUBLICATIONS

Translation of DE9002844.9 with translator's certificate dated Sep. 26, 2013 (cited in IPR 2013-00631, 2013-00632).
(Continued)

*Primary Examiner* — Charlotte M Baker
(74) *Attorney, Agent, or Firm* — Howard & Howard Attorneys PLLC

(57) ABSTRACT

A system for visualizing a surgical site is provided. The system includes a robotic mechanism for performing a procedure on a patient, an imaging device coupled to the robotic mechanism, the imaging device configured to provide image data of a site of interest, and a computing device coupled to the imaging device. The computing device includes one or more processors and at least one memory device configured to store executable instructions. The executable instructions, when executed by the processor, are configured to receive the image data of the site of interest, track motion patterns of the site of interest in the received image data, filter the received image data to remove line-of-sight restrictions therein and alter pixels therein based on the tracked motion patterns, and generate an output frame from the filtered image data. The system also includes a presentation interface device coupled to the computing device and configured to present the output frame for visualization of the site of interest.

17 Claims, 14 Drawing Sheets

Related U.S. Application Data

(60) Provisional application No. 62/369,821, filed on Aug. 2, 2016, provisional application No. 62/244,460, filed on Oct. 21, 2015.

(51) Int. Cl.
*G06T 7/20* (2017.01)
*A61B 34/30* (2016.01)
*A61B 90/00* (2016.01)
*G06T 19/00* (2011.01)
*G06T 7/11* (2017.01)
*G06T 7/194* (2017.01)
*A61B 90/98* (2016.01)

(52) U.S. Cl.
CPC ............... *G06T 7/11* (2017.01); *G06T 7/194* (2017.01); *G06T 7/20* (2013.01); *G06T 19/006* (2013.01); *A61B 90/98* (2016.02); *A61B 2034/2048* (2016.02); *A61B 2034/2055* (2016.02); *A61B 2034/2057* (2016.02); *A61B 2034/2065* (2016.02); *A61B 2090/365* (2016.02); *A61B 2090/376* (2016.02); *A61B 2090/378* (2016.02); *A61B 2090/392* (2016.02); *A61B 2090/3941* (2016.02); *G06T 2207/30008* (2013.01); *G06T 2207/30012* (2013.01); *G06T 2207/30016* (2013.01); *G06T 2210/41* (2013.01)

(58) Field of Classification Search
USPC ......................................................... 382/128
See application file for complete search history.

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,121,193 A | 12/1932 | Hanicke |
| 2,187,852 A | 8/1936 | Friddle |
| 2,178,840 A | 11/1936 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss |
| 3,347,234 A | 10/1967 | Voss |
| 3,367,809 A | 5/1968 | Soloff |
| 3,391,690 A | 7/1968 | Armao |
| 3,477,429 A | 11/1969 | Sampson |
| 3,513,848 A | 5/1970 | Winston |
| 3,518,993 A | 7/1970 | Blake |
| 3,577,991 A | 5/1971 | Wilkinson |
| 3,596,292 A | 8/1971 | Erb |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston |
| 3,678,980 A | 7/1972 | Gutshall |
| 3,709,218 A | 1/1973 | Halloran |
| 3,711,347 A | 1/1973 | Wagner |
| 3,739,773 A | 6/1973 | Schmitt |
| 3,760,808 A | 9/1973 | Bleuer |
| 3,788,318 A | 1/1974 | Kim |
| 3,789,852 A | 2/1974 | Kim |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,845,772 A | 11/1974 | Smith |
| 3,857,396 A | 12/1974 | Hardwick |
| 3,867,932 A | 2/1975 | Huene |
| 3,875,652 A | 4/1975 | Arnold |
| 3,898,992 A | 8/1975 | Balamuth |
| 3,918,442 A | 11/1975 | Nikolaev |
| 3,968,800 A | 7/1976 | Vilasi |
| 3,976,079 A | 8/1976 | Samuels |
| 4,023,559 A | 5/1977 | Gaskell |
| 4,064,566 A | 12/1977 | Fletcher |
| 4,089,071 A | 5/1978 | Kainberz |
| 4,108,399 A | 8/1978 | Pilgram |
| 4,156,574 A | 5/1979 | Boben |
| 4,164,794 A | 8/1979 | Spector |
| 4,171,544 A | 10/1979 | Hench |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogiu |
| 4,244,370 A | 1/1981 | Furlow |
| 4,257,411 A | 3/1981 | Cho |
| 4,265,231 A | 5/1981 | Scheller |
| 4,281,649 A | 8/1981 | Derweduwen |
| 4,291,698 A | 9/1981 | Fuchs |
| 4,309,488 A | 1/1982 | Heide |
| 4,320,762 A | 3/1982 | Bentov |
| 4,351,069 A | 9/1982 | Ballintyn |
| 4,364,381 A | 12/1982 | Sher |
| 4,365,356 A | 12/1982 | Broemer |
| 4,388,921 A | 6/1983 | Sutter |
| 4,395,798 A | 8/1983 | McVey |
| 4,409,974 A | 10/1983 | Freedland |
| 4,414,166 A | 11/1983 | Carlson |
| 4,437,362 A | 3/1984 | Hurst |
| 4,437,941 A | 3/1984 | Marwil |
| 4,444,180 A | 4/1984 | Schneider |
| 4,448,194 A | 5/1984 | DiGiovanni |
| 4,456,005 A | 6/1984 | Lichty |
| 4,461,281 A | 7/1984 | Carson |
| 4,493,317 A | 1/1985 | Klaue |
| 4,495,664 A | 1/1985 | Bianquaert |
| 4,501,031 A | 2/1985 | McDaniel |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins |
| 4,556,059 A | 12/1985 | Adamson |
| 4,556,350 A | 12/1985 | Bernhardt |
| 4,566,138 A | 1/1986 | Lewis |
| 4,589,868 A | 5/1986 | Dretler |
| 4,590,928 A | 5/1986 | Hunt |
| 4,597,379 A | 7/1986 | Kihn |
| 4,599,085 A | 7/1986 | Riess |
| 4,601,893 A | 7/1986 | Cardinal |
| 4,606,335 A | 8/1986 | Wedeen |
| 4,611,593 A | 9/1986 | Fogarty |
| 4,621,640 A | 11/1986 | Mulhollan |
| 4,630,609 A | 12/1986 | Chin |
| 4,632,101 A | 12/1986 | Freedland |
| 4,645,503 A | 2/1987 | Lin |
| 4,657,460 A | 4/1987 | Bien |
| 4,659,268 A | 4/1987 | Del Mundo |
| 4,662,063 A | 5/1987 | Collins |
| 4,662,068 A | 5/1987 | Polonsky |
| 4,662,887 A | 5/1987 | Turner |

(56) References Cited

U.S. PATENT DOCUMENTS

| | | |
|---|---|---|
| 4,669,473 A | 6/1987 | Richards |
| 4,681,107 A | 7/1987 | Kees |
| 4,685,458 A | 8/1987 | Leckrone |
| 4,691,741 A | 9/1987 | Affa |
| 4,705,040 A | 11/1987 | Mueller |
| 4,706,670 A | 11/1987 | Andersen |
| 4,708,139 A | 11/1987 | Dunbar |
| 4,713,077 A | 12/1987 | Small |
| 4,716,901 A | 1/1988 | Jackson |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble |
| 4,739,751 A | 4/1988 | Sapega |
| 4,741,330 A | 5/1988 | Hayhurst |
| 4,749,585 A | 6/1988 | Greco |
| 4,750,492 A | 6/1988 | Jacobs |
| 4,768,507 A | 9/1988 | Fischell |
| 4,772,286 A | 9/1988 | Goble |
| 4,776,328 A | 10/1988 | Frey |
| 4,776,738 A | 10/1988 | Winston |
| 4,776,851 A | 10/1988 | Bruchman |
| 4,781,182 A | 11/1988 | Purnell |
| 4,790,303 A | 12/1988 | Steffee |
| 4,792,336 A | 12/1988 | Hlavacek |
| 4,817,591 A | 4/1989 | Klause |
| 4,822,224 A | 4/1989 | Carl |
| 4,823,794 A | 4/1989 | Pierce |
| 4,832,025 A | 5/1989 | Coates |
| 4,832,026 A | 5/1989 | Jones |
| 4,834,752 A | 5/1989 | Vankampen |
| 4,841,960 A | 6/1989 | Garner |
| 4,843,112 A | 6/1989 | Gerhart |
| 4,846,812 A | 7/1989 | Walker |
| 4,862,812 A | 7/1989 | Walker |
| 4,862,882 A | 9/1989 | Venturi |
| 4,869,242 A | 9/1989 | Galluzo |
| 4,870,957 A | 10/1989 | Goble |
| 4,883,048 A | 11/1989 | Purnell |
| 4,890,612 A | 1/1990 | Kensey |
| 4,895,148 A | 1/1990 | Bays |
| 4,898,156 A | 2/1990 | Gattuma |
| 4,899,729 A | 2/1990 | Gill |
| 4,899,743 A | 2/1990 | Nicholson |
| 4,899,744 A | 2/1990 | Fujitsuka |
| 4,901,721 A | 2/1990 | Hakki |
| 4,921,479 A | 5/1990 | Grayzel |
| 4,922,897 A | 5/1990 | Sapega |
| 4,924,865 A | 5/1990 | Bays |
| 4,924,866 A | 5/1990 | Yoon |
| 4,932,960 A | 6/1990 | Green |
| 4,935,026 A | 6/1990 | McFadden |
| 4,935,028 A | 6/1990 | Drews |
| 4,945,625 A | 8/1990 | Winston |
| 4,946,468 A | 8/1990 | Li |
| 4,954,126 A | 9/1990 | Wallsten |
| 4,955,910 A | 9/1990 | Bolesky |
| 4,957,498 A | 9/1990 | Caspari |
| 4,961,741 A | 10/1990 | Hayhurst |
| 4,963,151 A | 10/1990 | Ducheyne |
| 4,964,862 A | 10/1990 | Arms |
| 4,966,583 A | 10/1990 | Debbas |
| 4,968,315 A | 11/1990 | Gattuma |
| 4,969,888 A | 11/1990 | Scholten |
| 4,969,892 A | 11/1990 | Burton |
| 4,979,949 A | 12/1990 | Matsen |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka |
| 5,009,652 A | 4/1991 | Morgan |
| 5,009,663 A | 4/1991 | Broome |
| 5,009,664 A | 4/1991 | Sievers |
| 5,013,316 A | 5/1991 | Goble |
| 5,019,090 A | 5/1991 | Pinchuk |
| 5,021,059 A | 6/1991 | Kensey |
| 5,031,841 A | 7/1991 | Schafer |
| 5,035,713 A | 7/1991 | Friis |
| 5,037,404 A | 8/1991 | Gold |
| 5,037,422 A | 8/1991 | Hayhurst |
| 5,041,093 A | 8/1991 | Chu |
| 5,041,114 A | 8/1991 | Chapman |
| 5,041,129 A | 8/1991 | Hayhurst |
| 5,046,513 A | 9/1991 | Gattuma |
| 5,047,055 A | 9/1991 | Gattuma |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Farnot |
| 5,078,140 A | 1/1992 | Kwoh |
| 5,078,731 A | 1/1992 | Hayhurst |
| 5,078,744 A | 1/1992 | Chvapil |
| 5,078,745 A | 1/1992 | Rhenter |
| 5,084,050 A | 1/1992 | Draenert |
| 5,084,051 A | 1/1992 | Tormala |
| 5,085,660 A | 2/1992 | Lin |
| 5,085,661 A | 2/1992 | Moss |
| 5,086,401 A | 2/1992 | Glassman |
| 5,090,072 A | 2/1992 | Kratoska |
| 5,098,433 A | 3/1992 | Freedland |
| 5,098,434 A | 3/1992 | Serbousek |
| 5,098,436 A | 3/1992 | Ferrante |
| 5,100,405 A | 3/1992 | McLaren |
| 5,100,417 A | 3/1992 | Cerier |
| 5,102,417 A | 4/1992 | Palmaz |
| 5,102,421 A | 4/1992 | Anspach |
| 5,120,175 A | 6/1992 | Arbegast |
| 5,123,520 A | 6/1992 | Schmid |
| 5,123,914 A | 6/1992 | Cope |
| 5,123,941 A | 6/1992 | Lauren |
| 5,133,732 A | 7/1992 | Wiktor |
| RE34,021 E | 8/1992 | Mueller |
| 5,141,520 A | 8/1992 | Goble |
| 5,147,362 A | 9/1992 | Goble |
| 5,152,765 A | 10/1992 | Ross |
| 5,154,720 A | 10/1992 | Trott |
| 5,156,613 A | 10/1992 | Sawyer |
| 5,156,616 A | 10/1992 | Meadows |
| 5,158,566 A | 10/1992 | Pianetti |
| 5,158,934 A | 10/1992 | Ammann |
| 5,163,960 A | 11/1992 | Bonutti |
| 5,171,251 A | 12/1992 | Bregen |
| 5,176,682 A | 1/1993 | Chow |
| 5,179,964 A | 1/1993 | Cook |
| 5,180,388 A | 1/1993 | DiCarlo |
| 5,183,464 A | 2/1993 | Dubrul |
| 5,192,287 A | 3/1993 | Fournier |
| 5,192,326 A | 3/1993 | Bao |
| 5,197,166 A | 3/1993 | Meier |
| 5,197,971 A | 3/1993 | Bonutti |
| 5,203,784 A | 4/1993 | Ross |
| 5,203,787 A | 4/1993 | Noblitt |
| 5,208,950 A | 5/1993 | Merritt |
| 5,209,776 A | 5/1993 | Bass |
| 5,217,486 A | 6/1993 | Rice |
| 5,217,493 A | 6/1993 | Raad |
| 5,219,359 A | 6/1993 | McQuilkin |
| 5,224,946 A | 7/1993 | Hayhurst |
| 5,226,899 A | 7/1993 | Lee |
| 5,230,352 A | 7/1993 | Putnam |
| 5,234,006 A | 8/1993 | Eaton |
| 5,234,425 A | 8/1993 | Fogarty |
| 5,236,438 A | 8/1993 | Wilk |
| 5,236,445 A | 8/1993 | Hayhurst |
| 5,242,902 A | 9/1993 | Murphy |
| 5,246,441 A | 9/1993 | Ross |
| 5,250,026 A | 10/1993 | Ehrlich |

(56) References Cited

U.S. PATENT DOCUMENTS

| | | |
|---|---|---|
| 5,250,055 A | 10/1993 | Moore |
| 5,254,113 A | 10/1993 | Wilk |
| 5,258,007 A | 11/1993 | Spetzler |
| 5,258,015 A | 11/1993 | Li |
| 5,258,016 A | 11/1993 | Di Poto |
| 5,261,914 A | 11/1993 | Warren |
| 5,266,325 A | 11/1993 | Kuzma |
| 5,269,783 A | 12/1993 | Sander |
| 5,269,785 A | 12/1993 | Bonutti |
| 5,269,809 A | 12/1993 | Hayhurst |
| 5,281,235 A | 1/1994 | Haber |
| 5,282,832 A | 2/1994 | Toso |
| 5,290,281 A | 3/1994 | Tschakaloff |
| 5,304,119 A | 4/1994 | Balaban |
| 5,306,280 A | 4/1994 | Bregen |
| 5,306,301 A | 4/1994 | Graf |
| 5,312,438 A | 5/1994 | Johnson |
| 5,315,741 A | 5/1994 | Dubberke |
| 5,318,588 A | 6/1994 | Horzewski |
| 5,320,611 A | 6/1994 | Bonutti |
| 5,324,308 A | 6/1994 | Pierce |
| 5,328,480 A | 7/1994 | Melker |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot |
| 5,330,486 A | 7/1994 | Wilkinson |
| 5,336,231 A | 8/1994 | Adair |
| 5,336,240 A | 8/1994 | Metzler |
| 5,339,799 A | 8/1994 | Kami |
| 5,343,385 A | 8/1994 | Joskowicz |
| 5,349,956 A | 9/1994 | Bonutti |
| 5,352,229 A | 10/1994 | Goble |
| 5,354,298 A | 10/1994 | Lee |
| 5,354,302 A | 10/1994 | Ko |
| 5,366,480 A | 11/1994 | Corriveau |
| 5,370,646 A | 12/1994 | Reese |
| 5,370,660 A | 12/1994 | Weinstein |
| 5,372,146 A | 12/1994 | Branchy |
| 5,374,235 A | 12/1994 | Ahrens |
| 5,376,126 A | 12/1994 | Lin |
| 5,382,254 A | 1/1995 | McGarry |
| 5,383,883 A | 1/1995 | Wilk |
| 5,383,905 A | 1/1995 | Golds |
| 5,391,171 A | 2/1995 | Schmieding |
| 5,391,173 A | 2/1995 | Wilk |
| 5,395,308 A | 3/1995 | Fox |
| 5,397,311 A | 3/1995 | Walker |
| 5,400,805 A | 3/1995 | Warren |
| 5,402,801 A | 4/1995 | Taylor |
| 5,403,312 A | 4/1995 | Yates |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker |
| 5,423,796 A | 6/1995 | Shikhman |
| 5,423,860 A | 6/1995 | Lizardi |
| 5,431,670 A | 7/1995 | Holmes |
| 5,411,538 A | 8/1995 | Bonutti |
| 5,438,746 A | 8/1995 | Demarest |
| 5,439,470 A | 8/1995 | Li |
| 5,441,502 A | 8/1995 | Bartlett |
| 5,441,538 A | 8/1995 | Bonutti |
| 5,443,512 A | 8/1995 | Parr |
| 5,447,503 A | 9/1995 | Miller |
| 5,449,372 A | 9/1995 | Schmaltz |
| 5,449,382 A | 9/1995 | Dayton |
| 5,451,235 A | 9/1995 | Lock |
| 5,453,090 A | 9/1995 | Martinez |
| 5,456,722 A | 10/1995 | McLeod |
| 5,458,653 A | 10/1995 | Davison |
| 5,462,561 A | 10/1995 | Voda |
| 5,464,424 A | 11/1995 | O'Donnell |
| 5,464,425 A | 11/1995 | Skiba |
| 5,464,426 A | 11/1995 | Bonutti |
| 5,464,427 A | 11/1995 | Curtis |
| 5,467,911 A | 11/1995 | Tsuruta |
| 5,470,337 A | 11/1995 | Moss |
| 5,472,444 A | 12/1995 | Huebner |
| 5,474,554 A | 12/1995 | Ku |
| 5,478,351 A | 12/1995 | Meade |
| 5,478,353 A | 12/1995 | Yoon |
| 5,480,403 A | 1/1996 | Lee |
| 5,486,197 A | 1/1996 | Le |
| 5,487,216 A | 1/1996 | Demarest |
| 5,487,844 A | 1/1996 | Fujita |
| 5,488,958 A | 2/1996 | Topel |
| 5,496,292 A | 3/1996 | Burnham |
| 5,496,335 A | 3/1996 | Thomason |
| 5,496,348 A | 3/1996 | Bonutti |
| 5,500,000 A | 3/1996 | Feagin |
| 5,501,700 A | 3/1996 | Hirata |
| 5,504,977 A | 4/1996 | Weppner |
| 5,505,735 A | 4/1996 | Li |
| 5,507,754 A | 4/1996 | Green |
| 5,514,153 A | 5/1996 | Bonutti |
| 5,518,163 A | 5/1996 | Hooven |
| 5,518,164 A | 5/1996 | Hooven |
| 5,520,700 A | 5/1996 | Beyar |
| 5,522,844 A | 6/1996 | Johnson |
| 5,522,845 A | 6/1996 | Wenstrom |
| 5,522,846 A | 6/1996 | Bonutti |
| 5,527,341 A | 6/1996 | Goglewski |
| 5,527,342 A | 6/1996 | Pietrzak |
| 5,527,343 A | 6/1996 | Bonutti |
| 5,528,844 A | 6/1996 | Johnson |
| 5,529,075 A | 6/1996 | Clark |
| 5,531,759 A | 7/1996 | Kensey |
| 5,534,012 A | 7/1996 | Bonutti |
| 5,534,028 A | 7/1996 | Bao |
| 5,540,703 A | 7/1996 | Barker |
| 5,540,718 A | 7/1996 | Bartlett |
| 5,542,423 A | 8/1996 | Bonutti |
| 5,545,178 A | 8/1996 | Kensey |
| 5,545,180 A | 8/1996 | Le |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,562,688 A | 10/1996 | Riza |
| 5,569,252 A | 10/1996 | Justin |
| 5,569,305 A | 10/1996 | Bonutti |
| 5,569,306 A | 10/1996 | Thal |
| 5,573,517 A | 11/1996 | Bonutti |
| 5,573,538 A | 11/1996 | Laboureau |
| 5,573,542 A | 11/1996 | Stevens |
| 5,575,801 A | 11/1996 | Habermeyer |
| 5,580,344 A | 12/1996 | Hasson |
| 5,584,835 A | 12/1996 | Greenfield |
| 5,584,860 A | 12/1996 | Goble |
| 5,584,862 A | 12/1996 | Bonutti |
| 5,591,206 A | 1/1997 | Moufarrege |
| 5,593,422 A | 1/1997 | Muijs Van De Moer |
| 5,593,425 A | 1/1997 | Bonutti |
| 5,593,625 A | 1/1997 | Riebel |
| 5,601,557 A | 2/1997 | Hayhurst |
| 5,601,558 A | 2/1997 | Torrie |
| 5,601,595 A | 2/1997 | Schwartz |
| 5,607,427 A | 3/1997 | Tschakaloff |
| 5,609,595 A | 3/1997 | Pennig |
| 5,618,314 A | 4/1997 | Harwin |
| 5,620,461 A | 4/1997 | Muijs Van De Moer |
| 5,626,612 A | 5/1997 | Bartlett |
| 5,626,614 A | 5/1997 | Hart |
| 5,626,718 A | 5/1997 | Phillippe |
| 5,628,446 A | 5/1997 | Geiste |
| 5,628,756 A | 5/1997 | Barker |
| 5,630,824 A | 5/1997 | Hart |
| 5,634,926 A | 6/1997 | Jobe |
| 5,628,751 A | 7/1997 | Sander |
| 5,643,272 A | 7/1997 | Haines |

(56) References Cited

U.S. PATENT DOCUMENTS

| | | |
|---|---|---|
| 5,643,274 A | 7/1997 | Sander |
| 5,643,293 A | 7/1997 | Kogasaka |
| 5,643,295 A | 7/1997 | Yoon |
| 5,643,320 A | 7/1997 | Lower |
| 5,643,321 A | 7/1997 | McDevitt |
| 5,645,553 A | 7/1997 | Kolesa |
| 5,645,597 A | 7/1997 | Krapiva |
| 5,645,599 A | 7/1997 | Samani |
| 5,649,940 A | 7/1997 | Hart |
| 5,649,955 A | 7/1997 | Hashimoto |
| 5,649,963 A | 7/1997 | McDevitt |
| 5,651,377 A | 7/1997 | O'Donnell |
| 5,658,313 A | 8/1997 | Thal |
| 5,660,225 A | 8/1997 | Saffran |
| 5,662,658 A | 9/1997 | Wenstrom |
| 5,665,089 A | 9/1997 | Dall |
| 5,665,109 A | 9/1997 | Yoon |
| 5,665,112 A | 9/1997 | Thal |
| 5,667,513 A | 9/1997 | Torrie |
| 5,669,917 A | 9/1997 | Sauer |
| 5,674,240 A | 10/1997 | Bonutti |
| 5,680,981 A | 10/1997 | Mililli |
| 5,681,310 A | 10/1997 | Yuan |
| 5,681,333 A | 10/1997 | Burkhart |
| 5,681,351 A | 10/1997 | Jamiolkowski |
| 5,681,352 A | 10/1997 | Clancy |
| 5,682,886 A | 11/1997 | Delp |
| 5,683,401 A | 11/1997 | Schmieding |
| 5,683,418 A | 11/1997 | Luscombe |
| 5,685,820 A | 11/1997 | Riek |
| 5,688,283 A | 11/1997 | Knapp |
| 5,690,654 A | 11/1997 | Ovil |
| 5,690,655 A | 11/1997 | Hart |
| 5,690,674 A | 11/1997 | Diaz |
| 5,690,676 A | 11/1997 | Dipoto |
| 5,693,055 A | 12/1997 | Zahiri |
| 5,697,950 A | 12/1997 | Fucci |
| 5,702,397 A | 12/1997 | Gonle |
| 5,702,462 A | 12/1997 | Oberlander |
| 5,707,395 A | 1/1998 | Li |
| 5,713,903 A | 2/1998 | Sander |
| 5,713,921 A | 2/1998 | Bonutti |
| 5,718,717 A | 2/1998 | Bonutti |
| 5,720,747 A | 2/1998 | Burke |
| 5,725,529 A | 3/1998 | Nicholson |
| 5,725,541 A | 3/1998 | Anspach |
| 5,725,556 A | 3/1998 | Moser |
| 5,725,582 A | 3/1998 | Bevan |
| 5,730,747 A | 3/1998 | Ek |
| 5,733,306 A | 3/1998 | Bonutti |
| 5,720,753 A | 4/1998 | Sander |
| 5,735,875 A | 4/1998 | Bonutti |
| 5,735,877 A | 4/1998 | Pagedas |
| 5,735,899 A | 4/1998 | Schwartz |
| 5,741,268 A | 4/1998 | Schutz |
| 5,741,282 A | 4/1998 | Anspach |
| 5,743,915 A | 4/1998 | Bertin |
| 5,748,767 A | 5/1998 | Raab |
| 5,752,952 A | 5/1998 | Adamson |
| 5,752,974 A | 5/1998 | Rhee |
| 5,755,809 A | 5/1998 | Cohen |
| 5,762,458 A | 6/1998 | Wang |
| 5,766,126 A | 6/1998 | Anderson |
| 5,766,221 A | 6/1998 | Benderev |
| 5,769,092 A | 6/1998 | Williamson, Jr. |
| 5,769,894 A | 6/1998 | Ferragamo |
| 5,772,672 A | 6/1998 | Toy |
| 5,776,136 A | 7/1998 | Sahay |
| 5,776,151 A | 7/1998 | Chan |
| 5,779,706 A | 7/1998 | Tschakaloff |
| 5,779,719 A | 7/1998 | Klein |
| 5,782,862 A | 7/1998 | Bonutti |
| 5,785,713 A | 7/1998 | Jobe |
| 5,792,096 A | 8/1998 | Rentmeester |
| 5,797,931 A | 8/1998 | Bito |
| 5,797,963 A | 8/1998 | McDevitt |
| 5,800,537 A | 9/1998 | Bell |
| 5,806,518 A | 9/1998 | Mittelstadt |
| 5,807,403 A | 9/1998 | Beyar |
| 5,810,849 A | 9/1998 | Kontos |
| 5,810,853 A | 9/1998 | Yoon |
| 5,810,884 A | 9/1998 | Kim |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey |
| 5,824,009 A | 10/1998 | Fukuda |
| 5,824,085 A | 10/1998 | Sahay |
| 5,830,125 A | 11/1998 | Scribner |
| 5,836,897 A | 11/1998 | Sakural |
| 5,839,899 A | 11/1998 | Robinson |
| 5,843,178 A | 12/1998 | Vanney |
| 5,844,142 A | 12/1998 | Blanch |
| 5,845,645 A | 12/1998 | Bonutti |
| 5,851,185 A | 12/1998 | Berns |
| 5,855,583 A | 1/1999 | Wang |
| 5,865,728 A | 2/1999 | Moll |
| 5,865,834 A | 2/1999 | McGuire |
| 5,866,634 A | 2/1999 | Tokushige |
| 5,868,749 A | 2/1999 | Reed |
| 5,873,212 A | 2/1999 | Esteves |
| 5,873,891 A | 2/1999 | Sohn |
| 5,874,235 A | 2/1999 | Chan |
| 5,876,325 A | 3/1999 | Mizuno |
| 5,879,371 A | 3/1999 | Gardiner |
| 5,879,372 A | 3/1999 | Bartlett |
| 5,891,166 A | 4/1999 | Schervinsky |
| 5,891,168 A | 4/1999 | Thal |
| 5,893,880 A | 4/1999 | Egan |
| 5,897,574 A | 4/1999 | Bonutti |
| 5,899,911 A | 5/1999 | Carter |
| 5,899,921 A | 5/1999 | Casparai |
| 5,906,579 A | 5/1999 | Vander Salm |
| 5,906,625 A | 5/1999 | Bito |
| 5,908,429 A | 6/1999 | Yoon |
| 5,911,449 A | 6/1999 | Daniele |
| 5,911,721 A | 6/1999 | Nicholson |
| 5,915,751 A | 6/1999 | Esteves |
| 5,918,604 A | 7/1999 | Whelan |
| 5,919,193 A | 7/1999 | Slavitt |
| 5,919,194 A | 7/1999 | Andersen |
| 5,919,208 A | 7/1999 | Valenti |
| 5,919,215 A | 7/1999 | Wiklund |
| 5,921,986 A | 7/1999 | Bonutti |
| 5,924,976 A | 7/1999 | Stelzer |
| 5,925,064 A | 7/1999 | Meyers |
| 5,928,244 A | 7/1999 | Tovey |
| 5,928,267 A | 7/1999 | Bonutti |
| 5,931,838 A | 8/1999 | Vito |
| 5,931,869 A | 8/1999 | Boucher |
| 5,937,504 A | 8/1999 | Esteves |
| 5,940,942 A | 8/1999 | Fong |
| 5,941,900 A | 8/1999 | Bonutti |
| 5,941,901 A | 8/1999 | Egan |
| 5,945,002 A | 9/1999 | Bonutti |
| 5,947,982 A | 9/1999 | Duran |
| 5,948,000 A | 9/1999 | Larsen |
| 5,948,001 A | 9/1999 | Larsen |
| 5,948,002 A | 9/1999 | Bonutti |
| 5,951,590 A | 9/1999 | Goldfarb |
| 5,956,927 A | 9/1999 | Daniele |
| 5,957,953 A | 9/1999 | Dipoto |
| 5,961,499 A | 10/1999 | Bonutti |
| 5,961,521 A | 10/1999 | Roger |
| 5,961,538 A | 10/1999 | Pedlick |
| 5,961,554 A | 10/1999 | Janson |
| 5,964,075 A | 10/1999 | Daniele |
| 5,964,765 A | 10/1999 | Fenton |
| 5,964,769 A | 10/1999 | Wagner |
| 5,967,970 A | 10/1999 | Cowan |
| 5,968,046 A | 10/1999 | Castleman |
| 5,968,047 A | 10/1999 | Reed |
| 5,970,686 A | 10/1999 | Demarest |
| 5,976,156 A | 11/1999 | Taylor |

(56) References Cited

U.S. PATENT DOCUMENTS

| | | |
|---|---|---|
| 5,980,520 A | 11/1999 | Vancaillie |
| 5,980,558 A | 11/1999 | Wiley |
| 5,980,559 A | 11/1999 | Bonutti |
| 5,983,601 A | 11/1999 | Blanch |
| 5,984,929 A | 11/1999 | Bashiri |
| 5,987,848 A | 11/1999 | Blanch |
| 5,989,282 A | 11/1999 | Bonutti |
| 5,993,458 A | 11/1999 | Vaitekunas |
| 5,993,477 A | 11/1999 | Vaitekunas |
| 6,007,567 A | 12/1999 | Bonutti |
| 6,007,580 A | 12/1999 | Lehto |
| 6,010,525 A | 1/2000 | Bonutti |
| 6,010,526 A | 1/2000 | Sandstrom |
| 6,012,216 A | 1/2000 | Esteves |
| 6,014,851 A | 1/2000 | Daniele |
| 6,017,321 A | 1/2000 | Boone |
| 6,032,343 A | 3/2000 | Blanch |
| 6,033,415 A | 3/2000 | Mittelstadt |
| 6,033,429 A | 3/2000 | Magovern |
| 6,033,430 A | 3/2000 | Bonutti |
| 6,045,551 A | 4/2000 | Bonutti |
| 6,050,998 A | 4/2000 | Fletcher |
| 6,056,751 A | 5/2000 | Fenton |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti |
| 6,059,827 A | 5/2000 | Fenton |
| 6,063,095 A | 5/2000 | Wang |
| 6,066,151 A | 5/2000 | Miyawaki |
| 6,066,160 A | 5/2000 | Colvin |
| 6,066,166 A | 5/2000 | Bischoff |
| 6,068,637 A | 5/2000 | Popov |
| 6,068,648 A | 5/2000 | Cole |
| 6,074,409 A | 6/2000 | Goldfarb |
| 6,077,277 A | 6/2000 | Mollenauer |
| 6,077,292 A | 6/2000 | Bonutti |
| 6,080,161 A | 6/2000 | Eaves |
| 6,081,981 A | 7/2000 | Demarest |
| 6,083,244 A | 7/2000 | Lubbers |
| 6,083,522 A | 7/2000 | Chu |
| 6,086,593 A | 7/2000 | Bonutti |
| 6,086,608 A | 7/2000 | Ek |
| 6,090,072 A | 7/2000 | Kratoska |
| 6,099,531 A | 8/2000 | Bonutti |
| 6,099,537 A | 8/2000 | Sugai |
| 6,099,547 A | 8/2000 | Gellman |
| 6,099,550 A | 8/2000 | Yoon |
| 6,099,552 A | 8/2000 | Adams |
| 6,102,850 A | 8/2000 | Wang |
| 6,106,545 A | 8/2000 | Egan |
| 6,117,160 A | 9/2000 | Bonutti |
| 6,120,536 A | 9/2000 | Ding |
| 6,125,574 A | 10/2000 | Ganaja |
| 6,126,677 A | 10/2000 | Ganaja |
| 6,132,368 A | 10/2000 | Cooper |
| 6,139,320 A | 10/2000 | Hahn |
| RE36,974 E | 11/2000 | Bonutti |
| 6,149,658 A | 11/2000 | Gardiner |
| 6,149,669 A | 11/2000 | Li |
| 6,152,949 A | 11/2000 | Bonutti |
| 6,155,756 A | 12/2000 | Mericle |
| 6,159,224 A | 12/2000 | Yoon |
| 6,159,234 A | 12/2000 | Bonutti |
| 6,171,307 B1 | 1/2001 | Orlich |
| 6,174,324 B1 | 1/2001 | Egan |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer |
| 6,190,401 B1 | 2/2001 | Green |
| 6,200,322 B1 | 3/2001 | Branch |
| 6,200,329 B1 | 3/2001 | Fung |
| 6,205,411 B1 | 3/2001 | Gigioia |
| 6,205,748 B1 | 3/2001 | Daniele |
| 6,217,591 B1 | 4/2001 | Egan |
| 6,224,593 B1 | 5/2001 | Ryan |
| 6,224,630 B1 | 5/2001 | Bao |
| 6,228,086 B1 | 5/2001 | Wahl |
| 6,231,565 B1 | 5/2001 | Tovey |
| 6,231,592 B1 | 5/2001 | Bonutti |
| 6,238,395 B1 | 5/2001 | Bonutti |
| 6,238,396 B1 | 5/2001 | Bonutti |
| 6,241,749 B1 | 6/2001 | Rayhanabad |
| 6,246,200 B1 | 6/2001 | Blumenkranz |
| 6,258,091 B1 | 7/2001 | Sevrain |
| 6,263,558 B1 | 7/2001 | Blanch |
| 6,264,675 B1 | 7/2001 | Brotz |
| 6,267,761 B1 | 7/2001 | Ryan |
| 6,273,717 B1 | 8/2001 | Hahn |
| 6,280,474 B1 | 8/2001 | Cassidy |
| 6,286,746 B1 | 9/2001 | Egan |
| 6,287,325 B1 | 9/2001 | Bonutti |
| 6,293,961 B2 | 9/2001 | Schwartz |
| 6,306,159 B1 | 10/2001 | Schwartz |
| 6,309,405 B1 | 10/2001 | Bonutti |
| 6,312,448 B1 | 11/2001 | Bonutti |
| 6,319,252 B1 | 11/2001 | McDevitt |
| 6,319,271 B1 | 11/2001 | Schwartz |
| 6,322,567 B1 | 11/2001 | Mittelstadt |
| 6,327,491 B1 | 12/2001 | Franklin |
| 6,331,181 B1 | 12/2001 | Tierney |
| 6,338,730 B1 | 1/2002 | Bonutti |
| 6,340,365 B2 | 1/2002 | Dittrich |
| 6,348,056 B1 | 2/2002 | Bates |
| 6,358,271 B1 | 3/2002 | Egan |
| 6,364,897 B1 | 4/2002 | Bonutti |
| 6,368,325 B1 | 4/2002 | McKinley |
| 6,368,326 B1 | 4/2002 | Dakin |
| 6,368,343 B1 | 4/2002 | Bonutti |
| 6,371,957 B1 | 4/2002 | Amrein |
| 6,385,475 B1 | 5/2002 | Cinquin |
| 6,395,007 B1 | 5/2002 | Bhatnagar |
| 6,409,742 B1 | 6/2002 | Fulton |
| 6,409,743 B1 | 6/2002 | Fenton |
| 6,419,704 B1 | 7/2002 | Ferree |
| 6,423,072 B1 | 7/2002 | Zappala |
| 6,423,088 B1 | 7/2002 | Fenton |
| 6,425,919 B1 | 7/2002 | Lambrect |
| 6,428,562 B2 | 8/2002 | Bonutti |
| 6,430,434 B1 | 8/2002 | Mittelstadt |
| 6,432,115 B1 | 8/2002 | Mollenauer |
| 6,436,107 B1 | 8/2002 | Wang |
| 6,447,516 B1 | 9/2002 | Bonutti |
| 6,447,550 B1 | 9/2002 | Hunter |
| 6,450,985 B1 | 9/2002 | Schoelling |
| 6,451,027 B1 | 9/2002 | Cooper |
| 6,461,360 B1 | 10/2002 | Adam |
| 6,468,265 B1 | 10/2002 | Evans |
| 6,468,293 B2 | 10/2002 | Bonutti |
| 6,471,715 B1 | 10/2002 | Weiss |
| 6,475,230 B1 | 11/2002 | Bonutti |
| 6,488,196 B1 | 12/2002 | Fenton |
| 6,496,003 B1 | 12/2002 | Okumura et al. |
| 6,500,195 B2 | 12/2002 | Bonutti |
| 6,503,259 B2 | 1/2003 | Huxel |
| 6,530,933 B1 | 3/2003 | Yeung |
| 6,533,157 B1 | 3/2003 | Whitman |
| 6,533,818 B1 | 3/2003 | Weber |
| 6,535,764 B2 | 3/2003 | Imran |
| 6,544,267 B1 | 4/2003 | Cole |
| 6,545,909 B2 | 4/2003 | Tanaka et al. |
| 6,547,792 B1 | 4/2003 | Tsuji |
| 6,551,304 B1 | 4/2003 | Whalen |
| 6,554,852 B1 | 4/2003 | Oberlander |
| 6,527,774 B2 | 5/2003 | Lieberman |
| 6,557,426 B2 | 5/2003 | Reinemann |
| 6,558,390 B2 | 5/2003 | Cragg |
| 6,562,043 B1 | 5/2003 | Chan |
| 6,565,554 B1 | 5/2003 | Niemeyer |
| 6,568,313 B2 | 5/2003 | Fukui |
| 6,569,167 B1 | 5/2003 | Bobechko |
| 6,569,187 B1 | 5/2003 | Bonutti |
| 6,572,635 B1 | 6/2003 | Bonutti |

(56) References Cited

U.S. PATENT DOCUMENTS

| | | | |
|---|---|---|---|
| D477,776 S | 7/2003 | Pontaoe |
| 6,585,746 B2 | 7/2003 | Gildenberg |
| 6,585,750 B2 | 7/2003 | Bonutti |
| 6,592,609 B1 | 7/2003 | Bonutti |
| 6,594,517 B1 | 7/2003 | Nevo |
| 6,585,764 B2 | 8/2003 | Wright |
| 6,605,090 B1 | 8/2003 | Trieu |
| 6,610,080 B2 | 8/2003 | Morgan |
| 6,618,910 B1 | 9/2003 | Pontaoe |
| 6,623,486 B1 | 9/2003 | Weaver |
| 6,623,487 B1 | 9/2003 | Goshert |
| 6,626,944 B1 | 9/2003 | Taylor |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer |
| 6,645,227 B2 | 11/2003 | Fallin |
| 6,666,877 B2 | 12/2003 | Morgan |
| 6,669,705 B2 | 12/2003 | Westhaver |
| 6,676,669 B2 | 1/2004 | Charles |
| 6,679,888 B2 | 1/2004 | Green |
| 6,685,750 B1 | 2/2004 | Plos |
| 6,699,177 B1 | 3/2004 | Wang |
| 6,699,240 B2 | 3/2004 | Francischelli |
| 6,702,821 B2 | 3/2004 | Bonutti |
| 6,705,179 B1 | 3/2004 | Mohtasham |
| 6,709,457 B1 | 3/2004 | Otte |
| 6,712,828 B2 | 3/2004 | Schraft |
| 6,714,841 B1 | 3/2004 | Wright |
| 6,719,765 B2 | 4/2004 | Bonutti |
| 6,719,797 B1 | 4/2004 | Ferree |
| 6,722,552 B2 | 4/2004 | Fenton |
| 6,731,988 B1 | 5/2004 | Green |
| 6,733,506 B1 | 5/2004 | McDevitt |
| 6,733,531 B1 | 5/2004 | Trieu |
| 6,764,514 B1 | 7/2004 | Li |
| 6,770,078 B2 | 8/2004 | Bonutti |
| 6,770,079 B2 | 8/2004 | Bhatnagar |
| 6,780,198 B1 | 8/2004 | Gregoire |
| 6,783,524 B2 | 8/2004 | Anderson |
| 6,786,989 B1 | 9/2004 | Torriani |
| 6,796,003 B1 | 9/2004 | Marvel |
| 6,799,065 B1 | 9/2004 | Niemeyer |
| 6,818,010 B2 | 11/2004 | Eichhorn |
| 6,823,871 B2 | 11/2004 | Schmieding |
| 6,827,712 B2 | 12/2004 | Tovey |
| 6,837,892 B2 | 1/2005 | Shoham |
| 6,840,938 B1 | 1/2005 | Morley |
| 6,843,403 B2 | 1/2005 | Whitman |
| 6,860,878 B2 | 3/2005 | Brock |
| 6,860,885 B2 | 3/2005 | Bonutti |
| 6,869,437 B1 | 3/2005 | Hausen |
| 6,878,167 B2 | 4/2005 | Ferree |
| 6,884,264 B2 | 4/2005 | Spiegelberg |
| 6,893,434 B2 | 5/2005 | Fenton |
| 6,899,722 B2 | 5/2005 | Bonutti |
| 6,890,334 B2 | 7/2005 | Brace |
| 6,913,666 B1 | 7/2005 | Aeschlimann |
| 6,916,321 B2 | 7/2005 | Tenhuisen |
| 6,921,264 B2 | 7/2005 | Mayer |
| 6,923,824 B2 | 8/2005 | Morgan |
| 6,932,835 B2 | 8/2005 | Bonutti |
| 6,942,684 B2 | 9/2005 | Bonutti |
| 6,944,111 B2 | 9/2005 | Nakamura |
| 6,951,535 B2 | 10/2005 | Ghodoussi |
| 6,955,540 B2 | 10/2005 | Mayer |
| 6,955,683 B2 | 10/2005 | Bonutti |
| 6,958,077 B2 | 10/2005 | Suddaby |
| 6,987,983 B2 | 1/2006 | Rosenblatt |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer |
| 7,013,191 B2 | 3/2006 | Rubbert |
| 7,018,380 B2 | 3/2006 | Cole |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan |
| 7,090,683 B2 | 8/2006 | Brock |
| 7,094,251 B2 | 8/2006 | Bonutti |
| 7,104,996 B2 | 9/2006 | Bonutti |
| 7,128,763 B1 | 10/2006 | Blatt |
| 7,147,652 B2 | 12/2006 | Bonutti |
| 7,153,312 B1 | 12/2006 | Torrie |
| 7,160,405 B2 | 1/2007 | Aeschlimann |
| 7,179,259 B1 | 2/2007 | Gibbs |
| 7,192,448 B2 | 3/2007 | Ferree |
| 7,209,776 B2 | 4/2007 | Leitner |
| 7,217,279 B2 | 5/2007 | Reese |
| 7,217,290 B2 | 5/2007 | Bonutti |
| 7,241,297 B2 | 7/2007 | Shaolian |
| 7,250,051 B2 | 7/2007 | Francischelli |
| 7,252,685 B2 | 8/2007 | Bindseil |
| 7,273,497 B2 | 9/2007 | Ferree |
| 7,297,142 B2 | 11/2007 | Brock |
| 7,329,263 B2 | 2/2008 | Bonutti |
| 7,331,932 B2 | 2/2008 | Leitner |
| 7,335,205 B2 | 2/2008 | Aeschlimann |
| 7,445,634 B2 | 11/2008 | Trieu |
| 7,477,926 B2 | 1/2009 | McCombs |
| 7,481,825 B2 | 1/2009 | Bonutti |
| 7,481,831 B2 | 1/2009 | Bonutti |
| 7,510,895 B2 | 3/2009 | Rateman |
| 7,641,660 B2 | 1/2010 | Lakin |
| 7,708,741 B1 | 5/2010 | Bonutti |
| 7,794,467 B2 | 9/2010 | McGinley |
| 7,831,295 B2 | 11/2010 | Friedrich |
| 7,854,750 B2 | 12/2010 | Bonutti |
| 7,879,072 B2 | 2/2011 | Bonutti |
| 7,891,691 B2 | 2/2011 | Bearey |
| 7,959,635 B1 | 6/2011 | Bonutti |
| 7,967,820 B2 | 6/2011 | Bonutti |
| 8,073,528 B2 * | 12/2011 | Zhao .................... B25J 9/1689 600/424 |
| 8,109,942 B2 | 2/2012 | Carson |
| 8,128,669 B2 | 3/2012 | Bonutti |
| 8,140,982 B2 | 3/2012 | Hamilton |
| 8,147,514 B2 | 4/2012 | Bonutti |
| 8,162,977 B2 | 4/2012 | Bonutti |
| 8,214,016 B2 | 7/2012 | Lavalee |
| 8,382,765 B2 | 2/2013 | Axelson |
| 8,429,266 B2 | 4/2013 | Vanheuverzwyn |
| 8,480,679 B2 | 7/2013 | Park |
| 8,483,469 B2 | 7/2013 | Pavlovskaia |
| 8,500,816 B2 | 8/2013 | Dees |
| 8,532,361 B2 | 9/2013 | Pavlovskaia |
| 8,560,047 B2 | 10/2013 | Haider |
| 8,617,171 B2 | 12/2013 | Park |
| 8,702,732 B2 | 4/2014 | Woodard |
| 8,715,291 B2 | 5/2014 | Park |
| 8,737,700 B2 | 5/2014 | Park |
| 8,777,875 B2 | 7/2014 | Park |
| 8,781,556 B2 | 7/2014 | Kienzle |
| 8,894,634 B2 | 11/2014 | Devengenzo |
| 8,968,320 B2 | 3/2015 | Park |
| 9,008,757 B2 | 4/2015 | Wu |
| 9,119,655 B2 | 9/2015 | Bowling |
| 9,456,765 B2 | 10/2016 | Odermatt |
| 2001/0002440 A1 | 5/2001 | Bonutti |
| 2001/0005975 A1 | 7/2001 | Golightly |
| 2001/0009250 A1 | 7/2001 | Herman |
| 2001/0041916 A1 | 11/2001 | Bonutti |
| 2001/0049497 A1 | 12/2001 | Kalloo |
| 2002/0016593 A1 | 2/2002 | Hearn |
| 2002/0016633 A1 | 2/2002 | Lin |
| 2002/0019649 A1 | 2/2002 | Sikora |
| 2002/0026244 A1 | 2/2002 | Trieu |
| 2002/0029083 A1 | 3/2002 | Zucherman |
| 2002/0029084 A1 | 3/2002 | Paul |
| 2002/0038118 A1 | 3/2002 | Shoham |
| 2002/0045888 A1 | 4/2002 | Ramans |
| 2002/0045902 A1 | 4/2002 | Bonutti |

(56) References Cited

U.S. PATENT DOCUMENTS

| | | |
|---|---|---|
| 2002/0049449 A1 | 4/2002 | Bhatnagar |
| 2002/0062136 A1 | 5/2002 | Hillstead |
| 2002/0062153 A1 | 5/2002 | Paul |
| 2002/0082612 A1 | 6/2002 | Moll |
| 2002/0087048 A1 | 7/2002 | Brock |
| 2002/0087049 A1 | 7/2002 | Brock |
| 2002/0087148 A1 | 7/2002 | Brock |
| 2002/0087166 A1 | 7/2002 | Brock |
| 2002/0087169 A1 | 7/2002 | Brock |
| 2002/0095175 A1 | 7/2002 | Brock |
| 2002/0103495 A1 | 8/2002 | Cole |
| 2002/0115934 A1 | 8/2002 | Tuke |
| 2002/0120252 A1 | 8/2002 | Brock |
| 2002/0123750 A1 | 9/2002 | Eisermann |
| 2002/0128633 A1 | 9/2002 | Brock |
| 2002/0128661 A1 | 9/2002 | Brock |
| 2002/0128662 A1 | 9/2002 | Brock |
| 2002/0133173 A1 | 9/2002 | Brock |
| 2002/0133174 A1 | 9/2002 | Charles |
| 2002/0133175 A1 | 9/2002 | Carson |
| 2002/0138082 A1 | 9/2002 | Brock |
| 2002/0138109 A1 | 9/2002 | Keogh |
| 2002/0143319 A1 | 10/2002 | Brock |
| 2002/0183762 A1 | 12/2002 | Anderson |
| 2002/0183851 A1 | 12/2002 | Spiegelberg |
| 2002/0188301 A1 | 12/2002 | Dallara |
| 2003/0014064 A1 | 1/2003 | Blatter |
| 2003/0028196 A1 | 2/2003 | Bonutti |
| 2003/0039196 A1 | 2/2003 | Nakamura |
| 2003/0040758 A1 | 2/2003 | Wang |
| 2003/0045900 A1 | 3/2003 | Hahnen |
| 2003/0055409 A1 | 3/2003 | Brock |
| 2003/0060927 A1 | 3/2003 | Gerbi |
| 2003/0065361 A1 | 4/2003 | Dreyfuss |
| 2003/0069591 A1 | 4/2003 | Carson |
| 2003/0105474 A1 | 6/2003 | Bonutti |
| 2003/0125808 A1 | 7/2003 | Hunter |
| 2003/0135204 A1 | 7/2003 | Lee |
| 2003/0153978 A1 | 8/2003 | Whiteside |
| 2003/0158582 A1 | 8/2003 | Bonutti |
| 2003/0167072 A1 | 8/2003 | Oberlander |
| 2003/0118518 A1 | 9/2003 | Hahn |
| 2003/0176783 A1 | 9/2003 | Hu |
| 2003/0181800 A1 | 9/2003 | Bonutti |
| 2003/0195530 A1 | 10/2003 | Thill |
| 2003/0195565 A1 | 10/2003 | Bonutti |
| 2003/0204204 A1 | 10/2003 | Bonutti |
| 2003/0212403 A1 | 11/2003 | Swanson |
| 2003/0216669 A1 | 11/2003 | Lang |
| 2003/0216742 A1 | 11/2003 | Wetzler |
| 2003/0225438 A1 | 12/2003 | Bonutti |
| 2003/0229361 A1 | 12/2003 | Jackson |
| 2004/0010287 A1 | 1/2004 | Bonutti |
| 2004/0030341 A1 | 2/2004 | Aeschlimann |
| 2004/0034282 A1 | 2/2004 | Quaid |
| 2004/4003435 | 2/2004 | Beane |
| 2004/0097939 A1 | 5/2004 | Bonutti |
| 2004/0097948 A1 | 5/2004 | Heldreth |
| 2004/0098050 A1 | 5/2004 | Foerster |
| 2004/0102804 A1 | 5/2004 | Chin |
| 2004/0106916 A1 | 6/2004 | Quaid |
| 2004/0138703 A1 | 7/2004 | Alleyne |
| 2004/0143334 A1 | 7/2004 | Ferree |
| 2004/0152970 A1 | 8/2004 | Hunter |
| 2004/0157188 A1 | 8/2004 | Luth |
| 2004/0167548 A1 | 8/2004 | Bonutti |
| 2004/0199072 A1 | 10/2004 | Sprouse |
| 2004/0220616 A1 | 11/2004 | Bonutti |
| 2004/0225325 A1 | 11/2004 | Bonutit |
| 2004/0230223 A1 | 11/2004 | Bonutti |
| 2004/0236374 A1 | 11/2004 | Bonutti |
| 2004/0236424 A1 | 11/2004 | Berez |
| 2004/0243109 A1 | 12/2004 | Tovey |
| 2004/0267242 A1 | 12/2004 | Grimm |
| 2005/0033366 A1 | 2/2005 | Cole |
| 2005/0038514 A1 | 2/2005 | Helm |
| 2005/0043796 A1 | 2/2005 | Grant |
| 2005/0071012 A1 | 3/2005 | Serhan |
| 2005/0090827 A1 | 4/2005 | Gedebou |
| 2005/0090840 A1 | 4/2005 | Gerbino |
| 2005/0096699 A1 | 5/2005 | Wixey |
| 2005/0113846 A1 | 5/2005 | Carson |
| 2005/0113928 A1 | 5/2005 | Cragg |
| 2005/0126680 A1 | 6/2005 | Aeschlimann |
| 2005/0143826 A1 | 6/2005 | Zucherman |
| 2005/0240227 A1 | 6/2005 | Bonutti |
| 2005/0149024 A1 | 7/2005 | Ferrante |
| 2005/0149029 A1 | 7/2005 | Bonutti |
| 2005/0177169 A1 | 8/2005 | Fisher |
| 2005/0192673 A1 | 9/2005 | Saltzman |
| 2005/0203521 A1 | 9/2005 | Bonutti |
| 2005/0216059 A1 | 9/2005 | Bonutti |
| 2005/0216087 A1 | 9/2005 | Zucherman |
| 2005/0222620 A1 | 10/2005 | Bonutti |
| 2005/0234332 A1 | 10/2005 | Murphy |
| 2005/0234461 A1 | 10/2005 | Burdulis |
| 2005/0234465 A1 | 10/2005 | McCombs |
| 2005/0240190 A1 | 10/2005 | Gall |
| 2005/0246021 A1 | 11/2005 | Ringelsen |
| 2005/0261684 A1 | 11/2005 | Shaolian |
| 2005/0267481 A1 | 12/2005 | Carl |
| 2005/0267534 A1 | 12/2005 | Bonutti |
| 2006/0009855 A1 | 1/2006 | Goble |
| 2006/0015101 A1 | 1/2006 | Warburton |
| 2006/0015108 A1 | 1/2006 | Bonutti |
| 2006/0024357 A1 | 2/2006 | Carpenter |
| 2006/0026244 A1 | 2/2006 | Watson |
| 2006/0064095 A1 | 3/2006 | Senn |
| 2006/0089646 A1 | 4/2006 | Bonutti |
| 2006/0122600 A1 | 6/2006 | Cole |
| 2006/0122704 A1 | 6/2006 | Vresilovic |
| 2006/0142657 A1 | 6/2006 | Quaid |
| 2006/0142799 A1 | 6/2006 | Bonutti |
| 2006/0161051 A1 | 7/2006 | Terrill-Grisoni |
| 2006/0161136 A1 | 7/2006 | Anderson |
| 2006/0167495 A1 | 7/2006 | Bonutti |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0235470 A1 | 10/2006 | Bonutti |
| 2006/0241695 A1 | 10/2006 | Bonutti |
| 2006/0265009 A1 | 11/2006 | Bonutti |
| 2006/0265011 A1 | 11/2006 | Bonutti |
| 2006/0271056 A1 | 11/2006 | Terrill-Grisoni |
| 2007/0032825 A1 | 2/2007 | Bonutti |
| 2007/0088340 A1 | 4/2007 | Brock |
| 2007/0088362 A1 | 4/2007 | Bonutti |
| 2007/0100258 A1 | 5/2007 | Shoham |
| 2007/0118055 A1 | 5/2007 | McCombs |
| 2007/0118129 A1 | 5/2007 | Fraser |
| 2007/0173946 A1 | 7/2007 | Bonutti |
| 2007/0185498 A2 | 8/2007 | Lavallee |
| 2007/0198555 A1 | 8/2007 | Friedman |
| 2007/0219561 A1 | 9/2007 | Lavallee |
| 2007/0239153 A1 | 10/2007 | Hodorek |
| 2007/0265561 A1 | 11/2007 | Yeung |
| 2007/0270833 A1 | 11/2007 | Bonutti |
| 2007/0287889 A1 | 12/2007 | Mohr |
| 2008/0021474 A1 | 1/2008 | Bonutti |
| 2008/0039845 A1 | 2/2008 | Bonutti |
| 2008/0039873 A1 | 2/2008 | Bonutti |
| 2008/0046090 A1 | 2/2008 | Paul |
| 2008/0097448 A1 | 4/2008 | Binder |
| 2008/0108897 A1 | 5/2008 | Bonutti |
| 2008/0108916 A1 | 5/2008 | Bonutti |
| 2008/0114399 A1 | 5/2008 | Bonutti |
| 2008/0132950 A1 | 6/2008 | Lange |
| 2008/0140088 A1 | 6/2008 | Orban |
| 2008/0140116 A1 | 6/2008 | Bonutti |
| 2008/0140117 A1 | 6/2008 | Bonutti |
| 2008/0195145 A1 | 8/2008 | Bonutti |
| 2008/0243127 A1 | 10/2008 | Lang |
| 2008/0249394 A1 | 10/2008 | Giori |

(56) References Cited

U.S. PATENT DOCUMENTS

| | | |
|---|---|---|
| 2008/0262812 A1 | 10/2008 | Arata |
| 2008/0269753 A1 | 10/2008 | Cannestra |
| 2008/0269808 A1 | 10/2008 | Gall |
| 2009/0024161 A1 | 1/2009 | Bonutti |
| 2009/0138014 A1 | 1/2009 | Bonutti |
| 2009/0093684 A1 | 4/2009 | Schorer |
| 2009/0131941 A1 | 5/2009 | Park |
| 2009/0194969 A1 | 8/2009 | Bearey |
| 2009/0197217 A1 | 8/2009 | Butscher |
| 2009/0287222 A1 | 11/2009 | Lee |
| 2010/0211120 A1 | 2/2010 | Bonutti |
| 2010/0217400 A1 | 8/2010 | Nortman |
| 2010/0256504 A1 | 10/2010 | Moreau-Gaudry |
| 2011/0029093 A1 | 2/2011 | Bojarski |
| 2011/0060375 A1 | 3/2011 | Bonutti |
| 2011/0082462 A1 | 4/2011 | Suarez |
| 2011/0087332 A1 | 4/2011 | Bojarski |
| 2011/0130761 A1 | 6/2011 | Plaskos |
| 2011/0144661 A1 | 6/2011 | Houser |
| 2011/0295253 A1 | 12/2011 | Bonutti |
| 2012/0053591 A1 | 3/2012 | Haines |
| 2012/0165841 A1 | 6/2012 | Bonutti |
| 2012/0184961 A1 | 7/2012 | Johannaber |
| 2012/0191140 A1 | 7/2012 | Bonutti |
| 2012/0215233 A1 | 8/2012 | Bonutti |
| 2012/0323244 A1 | 12/2012 | Cheal |
| 2012/0330429 A1 | 12/2012 | Axelson |
| 2013/0006267 A1 | 1/2013 | Odermatt |
| 2013/0035696 A1 | 2/2013 | Qutub |
| 2013/0072821 A1 | 3/2013 | Odermatt |
| 2013/0211531 A1 | 8/2013 | Steines |
| 2014/0257293 A1 | 9/2014 | Axelson |
| 2015/0106024 A1 | 4/2015 | Lightcap |
| 2015/0157416 A1 | 6/2015 | Andersson |
| 2015/0257768 A1 | 9/2015 | Bonutti |
| 2016/0012306 A1 | 1/2016 | Huan |
| 2016/0030115 A1 | 2/2016 | Shen |
| 2016/0081758 A1 | 3/2016 | Bonutti |
| 2016/0206375 A1 | 7/2016 | Abbasi |

FOREIGN PATENT DOCUMENTS

| | | |
|---|---|---|
| CA | 2698057 | 3/2009 |
| DE | 1903016 U | 10/1964 |
| DE | 1903316 U | 10/1964 |
| DE | 1903016 A1 | 8/1970 |
| DE | 3517204 | 11/1986 |
| DE | 3722538 | 1/1989 |
| DE | 9002844 U1 | 1/1991 |
| EP | 0784454 | 5/1996 |
| EP | 0773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 1991012779 | 9/1991 |
| WO | 199323094 | 11/1993 |
| WO | 1994008642 | 4/1994 |
| WO | 1995016398 | 6/1995 |
| WO | 1995031941 | 11/1995 |
| WO | 1996014802 | 5/1996 |
| WO | 1997012779 | 4/1997 |
| WO | 1997049347 | 12/1997 |
| WO | 1998011838 | 3/1998 |
| WO | 1998026720 | 6/1998 |
| WO | 2002053011 | 7/2002 |
| WO | 2007092869 | 8/2007 |
| WO | 2008116203 | 9/2008 |
| WO | 2009029908 | 3/2009 |
| WO | 2010099222 | 2/2010 |
| WO | 2015020093 | 2/2015 |

OTHER PUBLICATIONS

Declaration of Steve Jordan for U.S. Pat. No. 5,921,986, from IPR 2013-00632, dated Sep. 24, 2013 (exhibit 1010).

Declaration of Steve Jordan for U.S. Pat. No. 5,921,986, from IPR 2013-00633, dated Sep. 24, 2013 (exhibit 1007).

Declaration of Dr. Steve E. Jordan for U.S. Pat. No. 8,147,514, from IPR 2013-00631, dated Sep. 23, 2013.

The Search for the Holy Grail: A Century of Anterior Cruciate Ligament Reconstruction, R. John Naranja, American Journal of Orthopedics, Nov. 1997.

Femoral Bone Plug Recession in Endoscope Anterior Cruciate Ligament Reconstruction, David E. Taylor, Arthroscopy: The Journal of Arthroscopic and Related Surgery, Aug. 1996.

Meniscus Replacement with Bone Anchors: A Surgical Technique, Arthroscopy: The Journal of Arthroscopic and Related Surgery, 1994.

Problem Solving Report Question No. 1014984.066, Ultrasonic Welding, (c) 1999.

Guide to Ultrasound Plastic Assembly, Ultrasonic Division Publication, (c) 1995.

Branson, Polymers: Characteristics and Compatibility for Ultrasonic Assembly, Applied Technologies Group, Publication unknown.

Enabling Local Drug Delivery-Implant Device Combination Therapies, Surmodics, Inc., (c) 2003.

Stent Based Delivery of Sirolimus Reduces Neointimal Formation in a Porcine Coronary Model, Takeshi Suzuki, American Heart Association, Inc. (c) 2001.

Why Tie a Knot When You Can Use Y-Knot?, Innovasive Devices Inc., (c) 1998.

Ask Oxford, compact Oxford English dictionary: projection, Mar. 30, 2009.

Ask Oxford, compact Oxford English dictionary: slit, Mar. 30, 2009.

Textured Surface Technology, Branson Technology, Branson Ultrasonics Copr., (c) 1992.

Extended Search Report for 17183788.3, dated Oct. 5, 2017, 8 pages.

Gupta. "Dynamic illumination based system to remove the glare and improve the quality of medical images." Engineering in Medicine and Biology Society (EMBC), 2013 35th Annual International Conference of IEEE, pp. 3020-3023, Jul. 3, 2013.

WO2015020093 English Translation Sep. 4, 2017.

Arthrex, Protect your graft, Am J Sports Med, vol. 22, No. 4, Jul.-Aug. 1994.

Barrett et al, T-Fix endoscopic meniscal repair: technique and approach to different types of tears, Apr. 1995, Arthroscopy vol. 11 No. 2 p. 245-51.

Cope, Suture Anchor for Visceral Drainage, AJR, vol. 148 p. 160-162, Jan. 1986.

Gabriel, Arthroscopic Fixation Devices, Wiley Enc. of Biomed Eng., 2006.

Innovasive, We've got you covered, Am J Sports Med, vol. 26, No. 1, Jan.-Feb. 1998.

510k—TranSet Fracture Fixation System, Feb. 24, 2004, k033717.

510k—Linvatec Biomaterials modification of Duet and impact Suture Anchor, Nov. 19, 2004, k042966.

510k, Arthrex Pushlock, Jun. 29, 2005, K051219.

510k, Mitek Micro anchor, Nov. 6, 1996, K962511.

510k, Multitak Suture System, Jan. 10, 1997, K964324.

510k, Modified Mitek 3.5mm Absorbable Suture Anchor System, Jun. 9, 1997, K970896.

510K, Summary for Arthrex Inc.'s Bio-Interference Screw, Jul. 9, 1997, K971358.

510k, Surgicraft Bone Tie, Sep. 25, 1998, K982719.

(56) References Cited

OTHER PUBLICATIONS

Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64—Feb. 1998.
Packer et al, Repair of Acute Scapho-Lunate Dissociation Facilitated by the "TAG"* Suture Anchor, Journal of Hand Surgery (British and European Volume, 1994) 19B: 5: 563-564.
Richmond, Modification of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1Jan.-Feb. 1998: pp. 118-122.
Tfix, Acufexjust tied the knot . . . , Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 Feb. 2010: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger. et al, Radial avulsion of the triangular fibrocartilage complex in acute wrist trauma: a new technique for arthroscopic repair, Jun. 1997, Arthroscopy vol. 13 No. 3 p. 370-4.
Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al, Proximal Tibial Osteotomy for Osteoarthritis with Varus Deformity A Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of North America: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic Flatfoot and Skewfoot, J Bone Joint Surg,, 1195—p. 499-512.
Murphy et al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Petition for Inter Partes Review of U.S. Pat. No. 5,980,559, IPR 2013-00603, Filing Date Sep. 24, 2013.
Declaration of David Kaplan. Ph.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013,Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).
Translation of FR2696338 with translator's certificate dated Sep. 17, 2013 (cited in IPR 2013-00631, 2013-00632).

\* cited by examiner

SYSTEMS AND METHODS FOR NAVIGATION AND VISUALIZATION

CROSS-REFERENCE TO RELATED APPLICATIONS

This application claims the benefit of U.S. Provisional Application No. 62/244,460, filed Oct. 21, 2015, and U.S. Provisional Application 62/369,821, filed Aug. 2, 2016, each of which is hereby incorporated by reference in their entirety."

BACKGROUND

The field of the disclosure relates generally to visualization and navigation, and more specifically, to methods and systems for visualizing sites that do not have direct line of sight to a user.

Generally, clear visualization is important when performing detailed tasks such as driving, operating machinery, or performing surgery. For example, surgical procedures require direct line of site to prepare and conduct the surgical procedure to ensure accuracy. To reduce the complications during the surgical procedure, surgeons attempt to minimize any disturbances to body. Those disturbances can include minimal incisions that reduce the size surgical site, which in turn can limit the field of view for the surgeon. Accordingly, a need exists for visualization and navigation that provides feedback to a user (e.g., a physician/surgeon) while performing tasks (e.g., preoperatively, intraoperatively, and postoperatively) to increase the accuracy and efficiency of the task.

BRIEF DESCRIPTION

In one aspect, a robotic system for navigation of a surgical site is provided. The robotic system includes a computing device coupled to a presentation interface, a procedural component, and a communications interface. The computing device is also coupled to a first imaging device configured to provide imaging data of a surgical site. The computing device is also coupled to a second computing device that is configured to provide a second type of imaging data of the surgical site that is different that the imaging data of the first imaging device. The computing device is configured to co-register the imaging data to create a surgical site image for display to a surgeon on the presentation interface.

The features, functions, and advantages that have been discussed can be achieved independently in various embodiments or may be combined in yet other embodiments, further details of which can be seen with reference to the following description and drawings.

DETAILED DESCRIPTION

The systems and methods described herein enable accurate navigation during surgical procedures. The systems and methods described herein provide landmark information inside the body of a patient during a surgical procedure. As used herein, the term "tissue" or "body tissue" refers to a group or layer of similarly specialized cells that together perform certain special functions and can refer to any type of tissue in the body including, but not limed to, bone, organs, cartilage, muscles, skin, fat, nerves, and scars. As used herein the terms "procedure" or "surgery" refers to an operation performed on a patient to investigate and/or treat a pathological condition.

Figure 1:
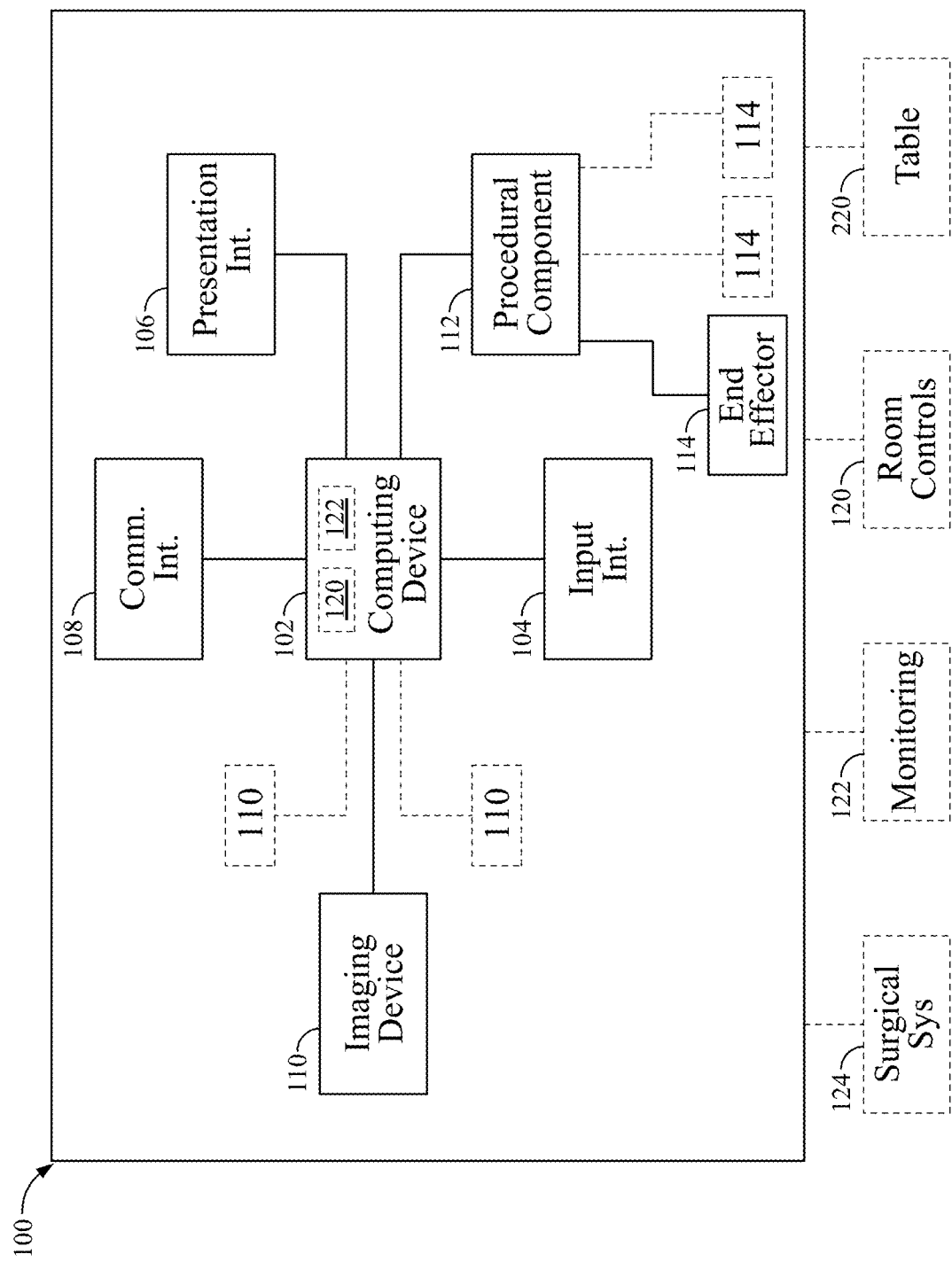
FIG. 1 is a block diagram of a robotic system 100 used in surgical procedures.

FIG. 1 is a block diagram of a robotic system 100 used in surgical procedures. System 100 includes a computing device 102, user input controls 104, a presentation interface 106, a communications interface 108, an imaging device 110, and a procedural component 112 having at least one end effector 114. In some embodiments, system 100 is communicatively coupled (e.g., through an electrical wire or cable, or wirelessly through Bluetooth or Wi-Fi) to additional operating room systems including, but not limited to, monitoring surgical room controls 120, surgical monitoring systems 122, and additional surgical systems 124 as well as an operating table or bed 220. The robotic system 100 could attach to the floor, be table mounted, and/or mounted to the patient. As further described herein, system 100 may be attached to or moving relative to the patient's body tissue. Moreover, system 100 could be a micro-robot that would be ingested or placed within the patient's body, including sensors that could communicate wirelessly and/or recharge via electromagnetic radiofrequency motion, ultrasound, capacitive coupling, and the like. Non-limiting examples of room controls 120 are HVAC (temperature, humidity), Oxygen, Nitrogen, Carbon Dioxide, and lighting and non-limiting examples of surgical monitoring systems 122 include cardiac, hemodynamic, respiratory, neurological, blood glucose, blood chemistry, organ function, childbirth, and body temperature monitoring. Additional surgical systems 124 include, but are not limited to, anesthesia (e.g., oxygen, carbon dioxide, nitrogen, nitrous oxide, etc.), endoscopy, arthroscopic, electromagnetic guidance, oncology, navigation, arthroscopy, tissue ablation, ultrasound ablation, cardiac, stent, valve, cardiovascular, ESW, inhalation, urologic, cerebrospinal fluid, synovial fluid, OB/GYN, ENG, neurosurgery, plastic surgery, pulmonary gastroenterology, and IV infusion systems. One having ordinary skill in the art will understand that system 100 may be used in a macroscopic manner and/or a microscopic manner, looking at cellular chemistry.

Computing device 102 includes at least one memory device 120 and one or more processors 122 (e.g., in a multi-core configuration) that is coupled to memory device 120 for executing instructions. In some embodiments, executable instructions are stored in memory device 120. Further, processor 122 may be implemented using one or more heterogeneous processor systems in which a main processor is present with secondary processors on a single chip. As another illustrative example, processor 122 may be a symmetric multi-processor system containing multiple processors of the same type. Processor 122 may perform partial processing and receive partial processing by a processor and/or computing device communicatively coupled to computing device 102 to enable cloud or remote processing. Further, processor 122 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. In the exemplary embodiment, processor receives imaging information from device 110 and creates co-registered images for display on interface 106 as well as providing movement limitations to component 112 based the imaging information.

In the exemplary embodiment, memory device 120 is one or more devices that enable information such as executable instructions and/or other data to be stored and retrieved. Memory device 120 may include one or more computer readable media, such as, without limitation, dynamic random access memory (DRAM), static random access memory (SRAM), a solid state disk, and/or a hard disk. Memory device 120 may be configured to store, without limitation, application source code, application object code, source code portions of interest, object code portions of interest, configuration data, execution events and/or any other type of data. In some embodiments, memory device 120 retains or stores limited or no information locally but stores information on a device communicatively coupled to system 100 to enable cloud storage.

In some embodiments, computing device 102 includes a presentation interface 106 that is coupled to processor 122. Presentation interface 106 presents information, such patient information and/or images (e.g. scans), to a user/surgeon. For example, presentation interface 106 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 106 includes one or more display devices. In the exemplary embodiment, presentation interface 106 displays surgical site data that is received from imaging device 110 and created by processor 122. The surgical site data may be displayed on presentation interface 106 and/or in any format that enables user view to surgical site information including but not limited to, glasses, a heads up display positioned within a surgical helmet, a retinal display that projects information onto the user's retina, and a monitor located within the operating room or some other remote location. In some embodiments, presentation interface 106 projects images from system 100 directly into the retina of a surgeon. In some embodiments, surgical site data is provided to the surgeon with audible commands to help direct the surgeon during a procedure.

In the exemplary embodiment, computing device 102 includes a user input interface 104. In the exemplary embodiment, user input interface 104 is coupled to processor 122 and receives input from a user/surgeon. User input interface 104 may include, for example, a keyboard, a pointing device, a mouse, a stylus, a touch sensitive panel (e.g., a touch pad or a touch screen), a gyroscope, an accelerometer, a position detector, and/or an audio user input interface. In some embodiments, user input interface 104 is a haptic feedback system that provides feedback (e.g. pressure, torque) from a procedural component 112. In some embodiments, a single component, such as a touch screen, may function as both a display device of presentation interface 106 and user input interface 104. In one or more embodiments, user input interface is a sensor that senses vibration, heat, thermal properties, and the like.

In one embodiment, user input interface 104 is one or more sensors coupled to a surgeon that are configured to detect muscle movement such that the procedural component 112 and/or end effector(s) 114 will respond to the detected muscle movements. In some embodiments, sensors are positioned on the skin of a surgeon or user so that the sensor can detect either mechanical (e.g., physical movement) or electrical signals of the muscles and/or nerves. Such a system enables a surgeon to perform a procedure remotely without the use of instrumentation directly coupled to the procedural component 112 and/or end effector 114. In some embodiments, a camera (i.e., imaging device 110) is utilized in conjunction with the sensors to determine and/or track surgeon movement patterns to provide a more efficient determination of surgeon movements.

In the exemplary embodiment, computing device 102 includes or is coupled to a communication interface 108 coupled to processor 122. Communication interface 108 communicates with imaging device 110, procedural component 112, and/or remote computing systems (not shown) such as mobile phones and/or tablets. To communicate with imaging device 110, procedural component 112, and/or remote computing systems, communication interface 108 may include, for example, a wired network adapter, a wireless network adapter (e.g. Bluetooth, Wi-Fi), and/or a mobile telecommunications adapter. In the exemplary embodiment, communication interface 108 and presentation interface 106 enable remote conferencing of a procedure with system 100. For example, a surgeon can receive guidance during a procedure from a remote surgeon, assistant, or medical sales representative during a procedure. Additionally, system 100 includes sensors of components 112 that sense movement of components and provide feedback to system 100 enabling system 100 to provide signals to provide tactile feedback and/or alarms to a surgeon through device in which the surgeon is interacting. Imaging device(s) 110 can provide remote users to visualize what is occurring in the procedure in real-time, while allowing the surgeon to interactively communicate with those remotely connected. Imaging device(s) 110 may also provide preoperative and/or postoperative images. Moreover, different types of imaging devices (e.g., fiberoptic, light, acoustic, laser, etc.) may be utilized intraoperatively.

Additionally, the remote conferencing described above can also be utilized to enable remote inventory management. For example, a medical device company or representative can utilize imaging device(s) 110 to view the inventory present in an operating room, or outside the operating room in a secure location (e.g., pharmacy, stock room), to determine what devices and/or objects have been utilized during a procedure. In some embodiments, an imaging device 110 (e.g., camera) scans an inventory system (e.g., cart) to determine, via processor 122, which objects are no longer present and were utilized during a procedure. It should be noted that system 100 can determine inventory levels by utilizing additional sensors. For example, in some embodiments, system 100 is coupled to a scale that weighs the inventory to determine missing items. In one embodiment, sensors are utilized to provide feedback to determine missing inventory based on displacement, an empty space in a known inventory location, and/or a changed shape of a stack or collection of inventory. Alternatively, system 100 is configured to track inventory using Automatic identification and data capture (AIDC) sensors configured to provide device information by receiving information from the inventory that includes, but it not limited to including, bar codes, Radio Frequency Identification (RFID), biometrics, magnetic stripes, Optical Character Recognition (OCR), smart cards, and voice recognition.

The device utilization is processed by system 100 and transmitted, via communication interface 108, to a hospital billing department, medical device supplier, practioner, clinic, and/or any other entity necessary to track device usage (e.g., insurance, procedure payor, and government reporting entity). It should be noted that system 100 is configured to track inventory systems within the medical and/or hospital including but not limited to, implants, surgical instruments, disposable medical devices, pharmaceuticals, and bracing. Additionally, the inventory control features described herein could be utilized by any system needing inventory control outside of the medical field.

In some embodiments, system 100 utilizes movement patterns for navigation (e.g., surgical navigation, vehicle navigation, etc.). In a surgical context, the actual movement or stimulation of tissue that twitches, moves, or goes in a motion pattern can be tracked by system 100 and used to navigate (i.e., understand where soft tissue is located relative to soft tissue and/or bone). For example, if electrical stimulation is used to stimulate a muscle or nerve to twitch, system 100 can track these movement patterns to determine where the nerve or muscle is located. In another exemplary embodiment, a spasm in the blood vessel can be created to determine where the blood vessel is located to create patterns of navigation. System 100 can also be used at a microscopic level to create navigation at a cellular level where cell membranes and/or cell receptors are stimulated. As movement patterns are tracked, system 100, using methods described herein, could remove pixels and/or enhance or change a visualization. For example, if tissue, cells, and/or membranes are stimulated to move, system 100 could eliminate or remove those pixels In some embodiments, aspects of system 100 utilize extensor optical systems. Numerous optical sensors are known to those of ordinary skill in the art. For example, if there are opacities in the way of the optical sensor such as cloudiness, bleeding, or synovial fluid, an optical sensor may inaccurately note properties, such as pH or pressure. By removing opacities, system 100 improves the functioning of the optical sensors. In some embodiments, system 100 changes light to color the frequency or intensity by strobing, flashing on/off, and/or displaying different intensities as it reflects (i.e., albedo). System 100 may also remove tissues that reflect differently based on light color, frequency, intensity, and/or strobe.

Figure 2:
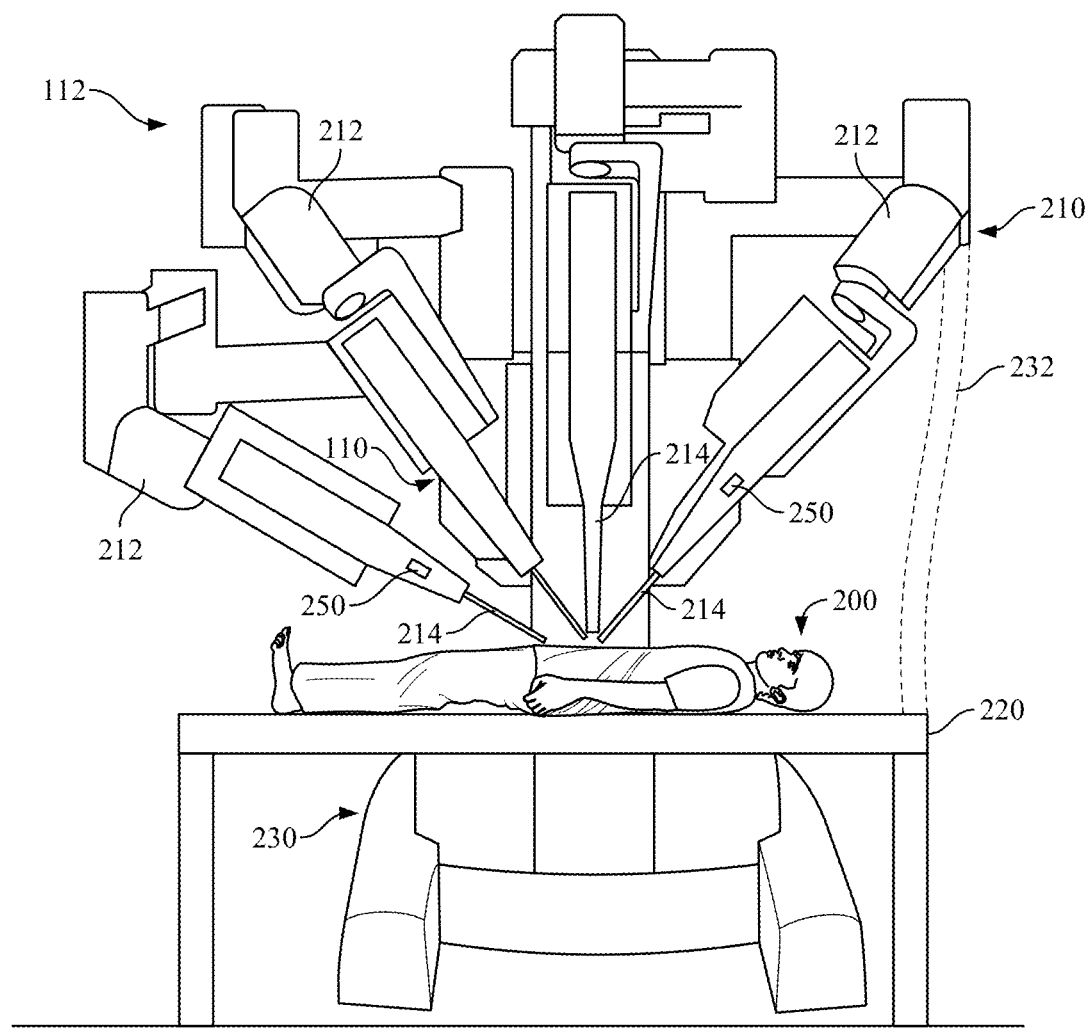
FIG. 2 is a perspective of an exemplary procedural component that may be used with the system shown in FIG. 1.
Figure 3:
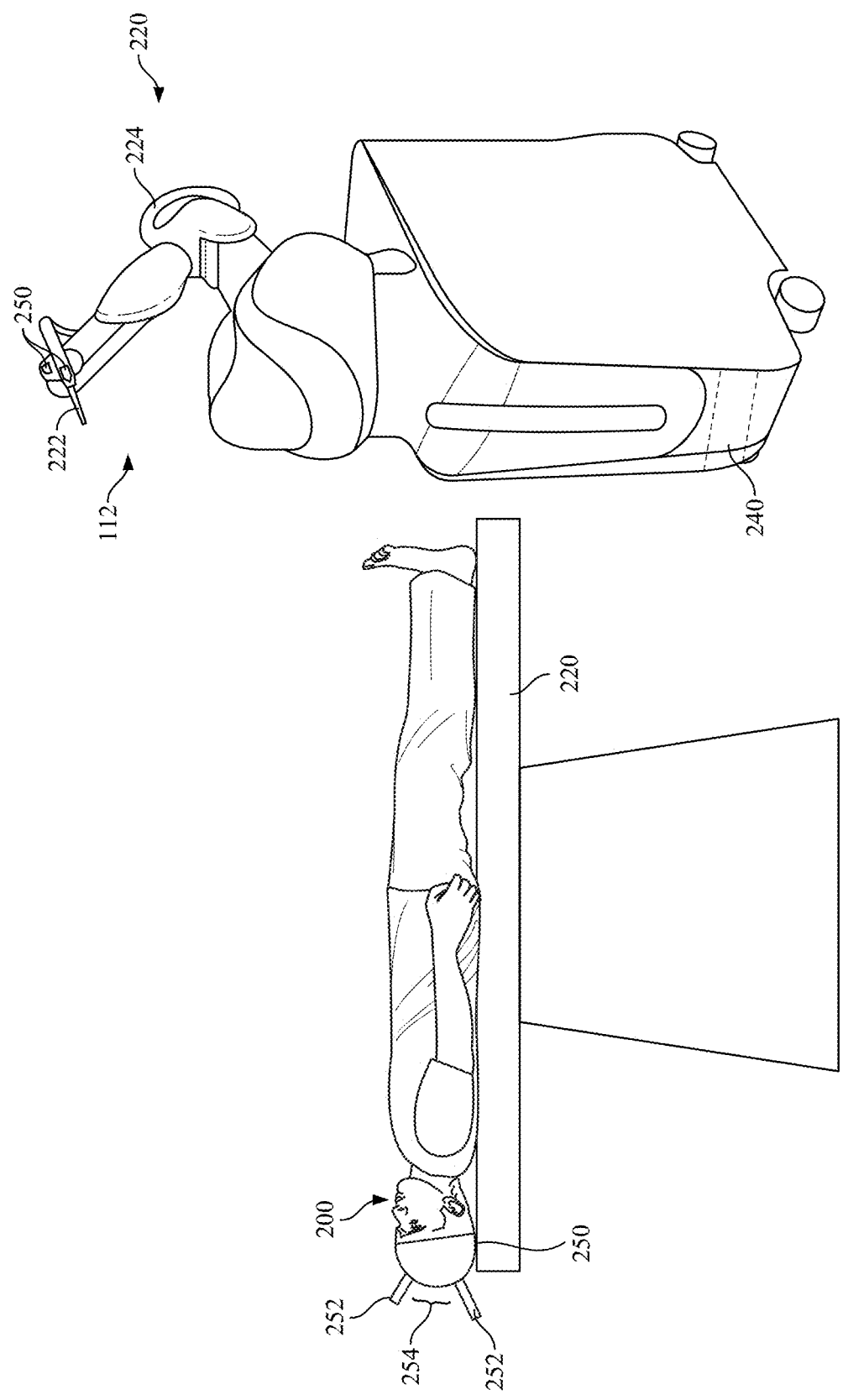
FIG. 3 is a perspective of an alternative procedural component that may be used with the system shown in FIG. 1.
Figure 4:
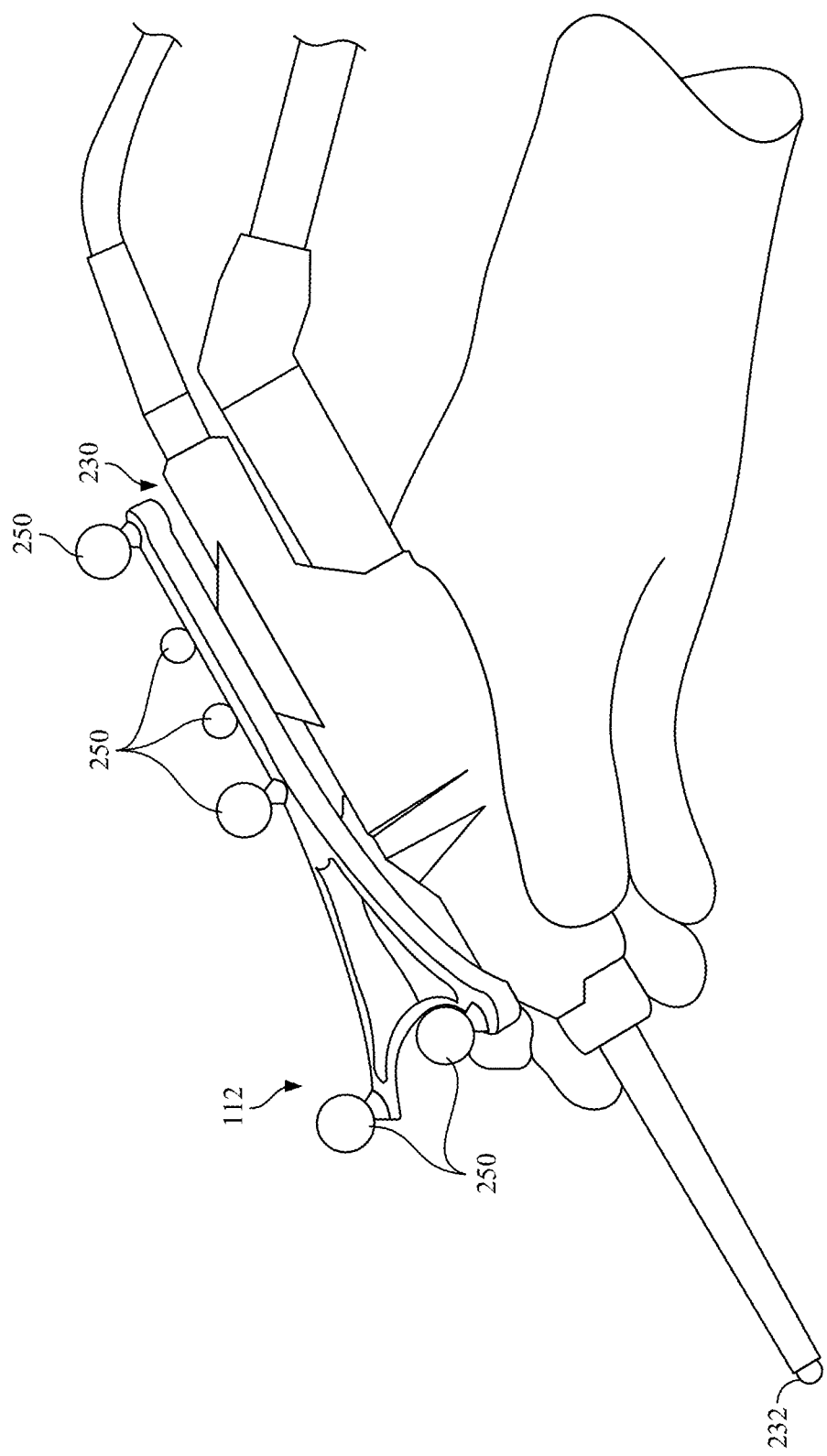
FIG. 4 is a perspective of an alternative procedural component that may be used with the system shown in FIG. 1.

FIGS. 2-4 are schematic diagrams of exemplary procedural components 210, 230, and 250 that may be used with system 100, shown in FIG. 1. FIG. 2 is a schematic diagram of an exemplary procedural component 112 in the form of a telemanipulator 210. Telemanipulator 210 receives operational instructions from a user/surgeon operating input interface 104. In such an embodiment, the user/surgeon is capable of performing normal surgical movements while arms 212 carry out those movements using end-effectors and manipulators 214 to perform the actual surgery on the patient 200. It should be noted that utilizing a telemanipulator 210, the surgeon does not have to be present in the operating room, but can be anywhere in the world, leading to the possibility for remote surgery. In some embodiments, telemanipulator 210 includes an imaging device 110 (e.g. endoscope) within an arm 214.

FIG. 3 is a schematic diagram of an alternative procedural component 112 in the form of a user movable robotic arm 220. In the exemplary embodiment, a surgeon manipulates arm 220 by moving an end effector 222 into place by movement of handle portion 224. During a procedure, the surgeon utilizes arm 220 and more specifically end effector 222 with limitations that are imposed by computing device 102 and/or processor 122 with information obtained from imaging device 110.

FIG. 4 is a schematic diagram of an alternative procedural component 112 in the form of a manual surgical tool 230. In such an embodiment, tool 230 is manufactured to be portable (i.e. hand-held) such that the surgeon can manipulate the tool 230 during a procedure. Tool 230 includes an end effector 232 capable of performing surgical functions on a patient. In an embodiment, tool 230 can be at least partially sterilized. In another embodiment, tool 230 includes surgical drains that cover part of tool 230 and sterilize parts in an operating room, such as sleeves, drapes, and the like.

It should be noted that system 100 is configured to complete an entire surgical procedure utilizing only system 100, inclusive of the procedural component 112 which non-limiting examples are represented by telemanipulator 210, arm 220, and tool 230. As noted above, procedural component may include one or more end effectors 214, 222, and 232 to perform to actions needed to perform the surgical procedure. The actions of component 112 can be any surgical action including, but not limited to, sewing, stitching, stapling, cutting, sawing, cauterizing, grasping, pinching, holding, tensioning, moving, implanting, removing, viewing, sensing force, sensing pressure, and tying. The end effectors 214, 222, and 232 can be any end effector needed for performing the surgical actions including, but not limited to, forceps, needles, needle drivers, retractors, clip appliers, probe graspers, cardiac stabilizers, balloons, tissue dissectors, saws, knives, mills, reamers, coagulation devices, lasers, ultrasonic transducers/probes, cautery instruments, scalpels, staplers, scissors, graspers, and sealers.

Figure 5:
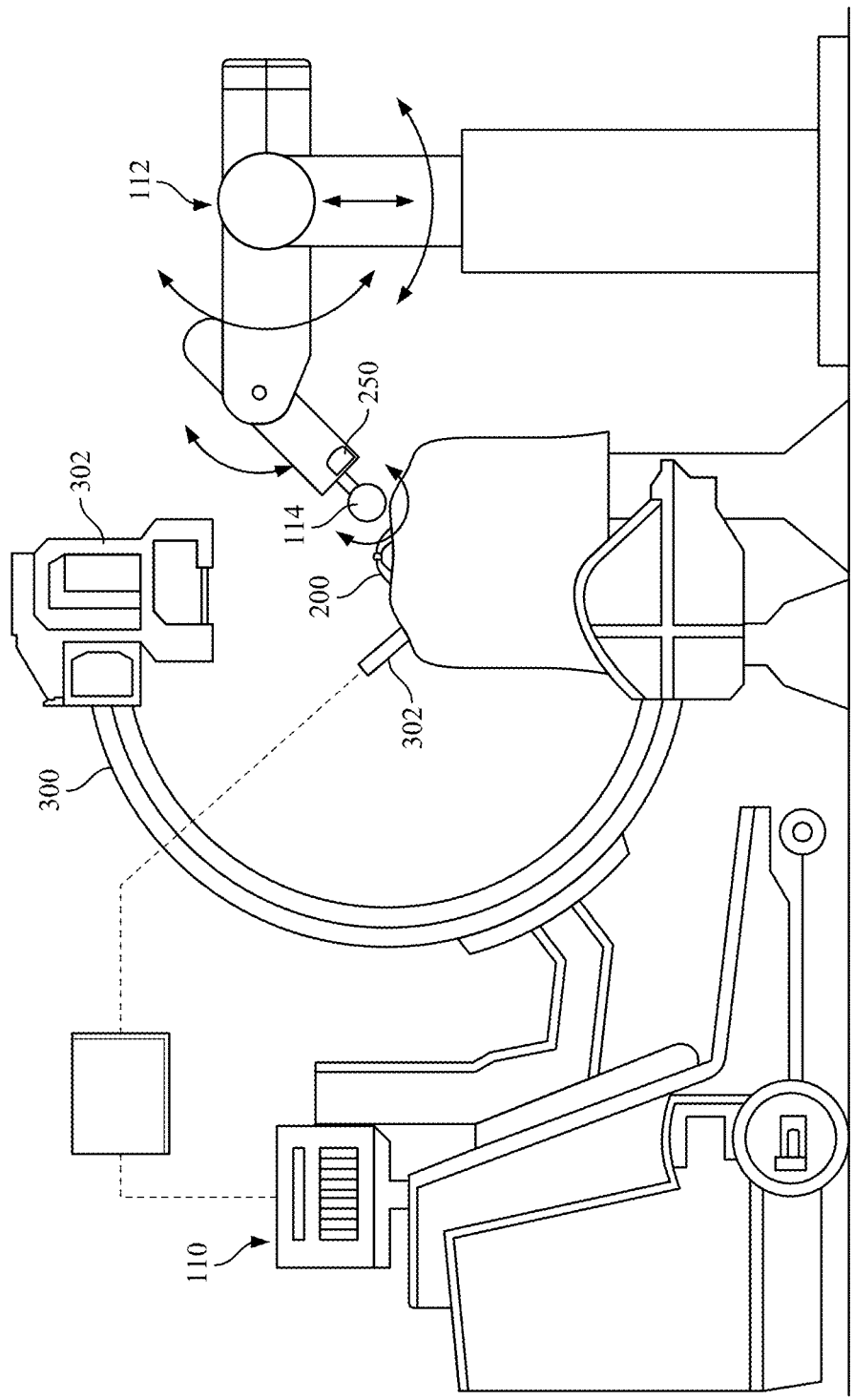
FIG. 5 is a perspective of a patient undergoing a procedure using the system shown in FIG. 1.

In the exemplary embodiment, system 100 includes at least one imaging device 110. As shown in FIG. 5, imaging device 110 can substantially surround or be positioned adjacent patient 200 undergoing a procedure (i.e., intraoperative) performed at least in part by procedural component 112 and/or end effector 114. In the exemplary embodiment, imaging device 110 includes a C-arm 300 coupled to a scanner 302. In one embodiment, scanner 302 is a gamma camera configured to detect radioactive tracers inside the body of patient 200. Alternatively, scanner 302 is any device that is capable of scanning and/or detecting environmental information of patient 200, a surgical site, and/or and operating room including, but not limited to, endoscopy, fluoroscopy (e.g. X-ray, CT, CAT scan), laser or ultrasonic Doppler velocimetry, projection radiography, MRI, SPECT, PET, ultrasound, infrared, elastography, tactile imaging, photoacoustic imaging, thermography, tomography, echocardiography, NIRS, and fNIRS. In an embodiment, environmental information scanned and/or detected via a plurality of techniques may be combined (e.g., combining visible light wavelengths and infrared for imaging technologies). In some embodiments, imaging device 110 may have one or more scanners 302 located at, near, adjacent, or in a surgical site to perform imaging. In one embodiment, imaging device 110 includes a scanner 302 that is configured to locate procedural component markers 250 positioned on procedural components 112. Marker 250 information is transmitted to computing device 102 to determine component location relative to patient 200, other components of system 100, and/or the operating room. In the exemplary embodiment, system 100 includes an imaging device 110 that provides holistic imaging of a surgical site to provide users with the necessary imaging to complete a procedure. For example, in a knee arthroplasty procedure, the imagine device(s) 110 used in the procedure would provide the surgeon images of the knee as well as relative joints (e.g., hip and ankle) to ensure an effective procedure. In such a procedure, system 100 would produce a three dimensional model of the hip, knee, and ankle to provide views of the procedure in all angles including anterior-posterior (AP) views and medial-lateral (ML) views. While a non-limiting example of an arthroplasty procedure is provided, it should be noted that the holistic imaging could be utilized with any type of procedure utilizing system 100.

In preparation for use of the robotic system 100, a calibration is required to ensure that accuracy of the end effectors 114. Typically, imaging (e.g. CT) of the patient is done preoperatively and the images are loaded into system 100. In some instances, during the calibration of system 100, while patient 200 is in the operating room and on the operating table, patient markers are placed or pinned into the body to provide landmark information. The system 100 is configured to associate the patient landmark information with the images provided preoperatively to provide a map of a surgical site as shown in FIG. 9.

In some embodiments, calibration is aided by coupling the robotic system to the surgical table and/or the patient. Coupling system 100 to a surgical table or bed provides system 100 relative patient position information as the patient is moved during a procedure. Referring to FIG. 2, procedural component 112 can be configured to couple directly to table 220 at a base 230 of telemanipulator 210 or at or near arm(s) 212 of telemanipulator 210 via coupling mechanism 232. Referring to FIG. 3, movable robotic arm 220 can be configured to have one or more recesses or docks 240 provided within arm 220 to couple directly into table 220. In addition to being coupled to table 220. Components 112 can be coupled directly to the patient. In some embodiments, custom molded or 3-D printed devices 250 can be created for each patient to be worn during a procedure. To create such devices 250, preoperative scans are taken of a surgical site and custom fit devices 250 would be manufactured to be placed on the patient. In one such non-limiting example, as is shown in FIG. 3, for a brain surgery, a helmet 250 is custom manufactured for patient 200 and includes attachment portions 252 that provide a coupling point for components 112 as well as apertures 254 for performing the procedure. Devices 250 can be manufactured to fit any body portion undergoing a procedure including, but not limited to, an abdomen, leg, knee, foot, ankle, neck, back, torso, arm, hand, head, and face.

It should be noted that procedural components can be configured to dock or electrically couple into surgical tables or beds such that communication from each can be transmitted back and forth via a communications interface. In some embodiments, procedural components 112 rigidly couple to the table or bed while other embodiments provide an electrical wire, cable, or wireless (e.g., Bluetooth or Wi-Fi) coupling between the components 112 and the table. In addition, in some embodiments, procedural components 112 rigidly couple directly to a patient or to surgical instrumentations utilized during a procedure (e.g., surgical robot, instrumentation, visualization system, retractor, electrosurgery system, knife, saw, and mill). In some embodiments, procedural components 112 are used in a transmitter/physician office or other locations such as insurance companies and the like.

In the exemplary embodiment, a radioactive tracer is inserted into the body and landmark information of the patient is determined by a radioactive detector (e.g. scanner 302) of system 100 and provided to a surgeon via presentation interface 106 to increase the efficiency and accuracy of the procedure. As is commonly known, radioactive tracers emit gamma rays from within the body. These tracers are generally short-lived isotopes linked to chemical compounds (e.g. radiopharmaceutical) that enable examination of specific physiological processes and/or anatomical landmarks. In some embodiments, the tracers are given through an intravenous injection (e.g. IV), inhalation, or orally. In some embodiments, the tracers are optical and/or biodegradable.

In the exemplary embodiment, Technecium-99m is used as the radioactive tracer. Technetium-99m emits 140 kev gamma rays with a half-life of approximately 6 hours that exits in the form of pertechnetiate ion (TcO4). Alternatively, any radioactive tracer could be used with the systems and methods described herein, including but not limited to, Bismuth-213, Calcium-47, Carbon-11, Cesium-137, Chromium-51, Cobalt-57, Cobalt-60, Copper-67, Dysprosium-165, Erbium-169, Fluorine-18, Gallium-67, Holmium-166, Indium-111, Iodine-123, Iodine-125, Iodine-131, Iridium-192, Iron-59, Irridium-192, Krypton-81m, Lutetium-177, Molybdenum-99, Nitrogen-13, Oxygen-15, Palladium-103, Phosphorus-32 & 33, Potassium-42, Rhenium-186, Rhenium-188, Rubidium-82, Samarium-153, Selenium-75, Sodium-24, Strontium-85, Strontium-89, Strontium-92, Sulfur-35, Technecium-99m, Thallium-201, Uranium-235, Xenon-133, Ytterbium-169, and Yttrium-90.

In some embodiments, the tracers are detected by a gamma camera, which recognize photons enabling a view of internal landmarks of a patient from many different angles. In such an embodiment, the camera builds up an image from the points from which radiation is emitted and the image is enhanced by system 100 and viewed by a physician on monitor 106. In an alternative embodiment, a Positron Emission Tomography (PET) is performed in which a PET camera detects emission of two identifiable gamma rays in opposite directions to identify landmarks. In yet another embodiment, myocardial perfusion imaging (MPI) is performed to identify landmarks. In some embodiments, images having landmarks identified with tracers (e.g. gamma, PET, MPI) are utilized with a computerized tomography (CT) scan and the images are co-registered (e.g. layered) by system 100 to provide complete landmark information. It should be noted that the tracer images can be co-registered with any other type of imaging (e.g. ultrasound, x-ray, and MRI) to produce landmark information. In an embodiment, the tracers are used for ultrasound navigation with or without radiation. The ultrasound navigation may be utilized for surface mapping or registering anatomical data points.

During robot assisted surgery, such as surgery utilizing system 100, it is necessary to have multiple fixed points for recognition by trackers to allow for navigational computation. Currently, in the case of arthroplasty, invasive pins are inserted into the bones to calibrate the robotic system and to create landmarks. In the exemplary embodiment, the landmark information found via tracers is utilized for calibration and navigational computation. In such an embodiment, after the radiopharmaceutical (e.g. technetium) is introduced into the system, the tracer is taken up by osteoblasts and noted on resulting images. Often, the tracer appears dark on an image and can be known as a hot spot. These locations are co-registered with other images, by system 100 and the system 100 performs calculations using known algorithms to determine key distances and/or boundary layers for surgery.

Figure 6A:
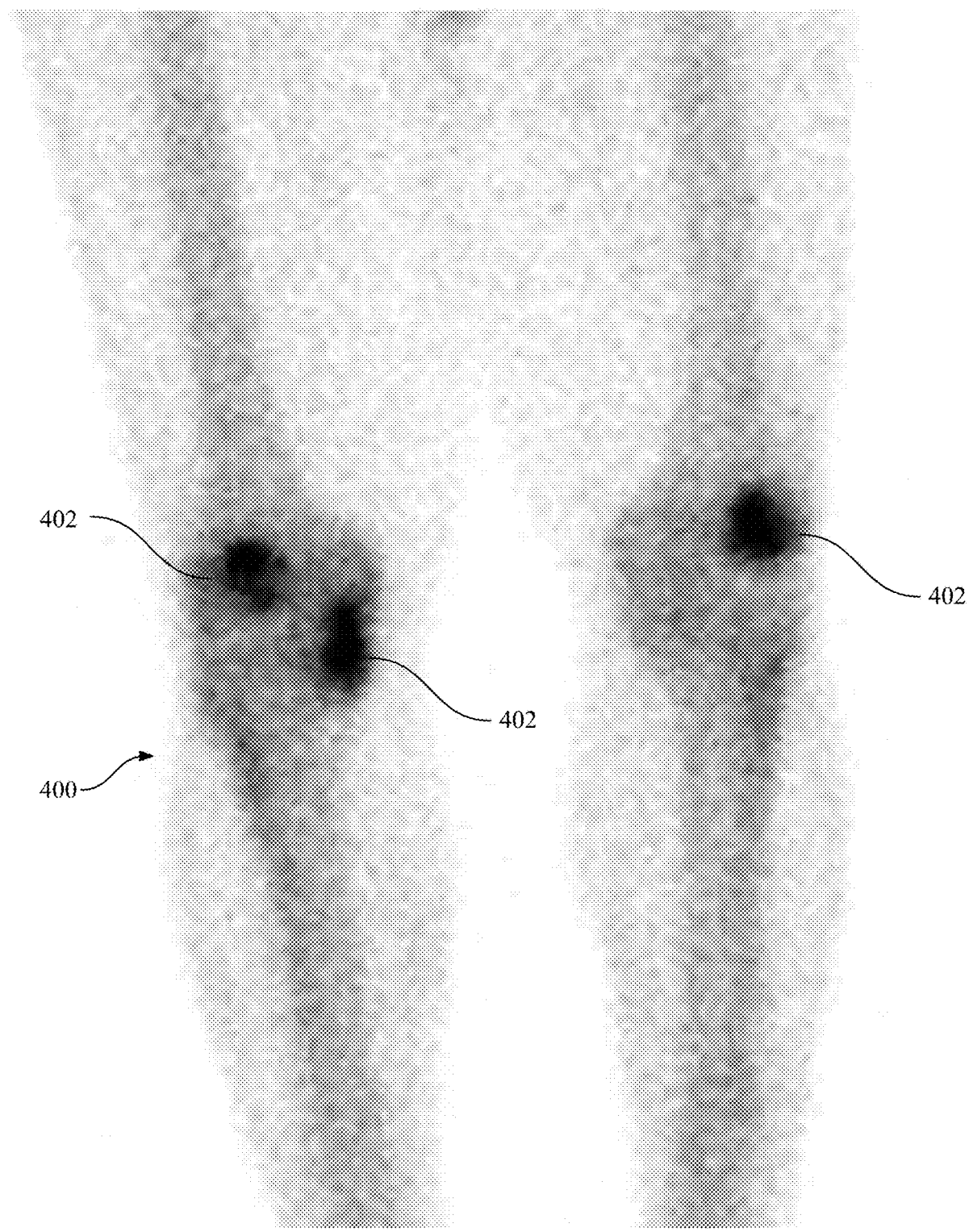
FIGS. 6A and 6B are exemplary images produced by the system shown in FIG. 1.
Figure 6B:
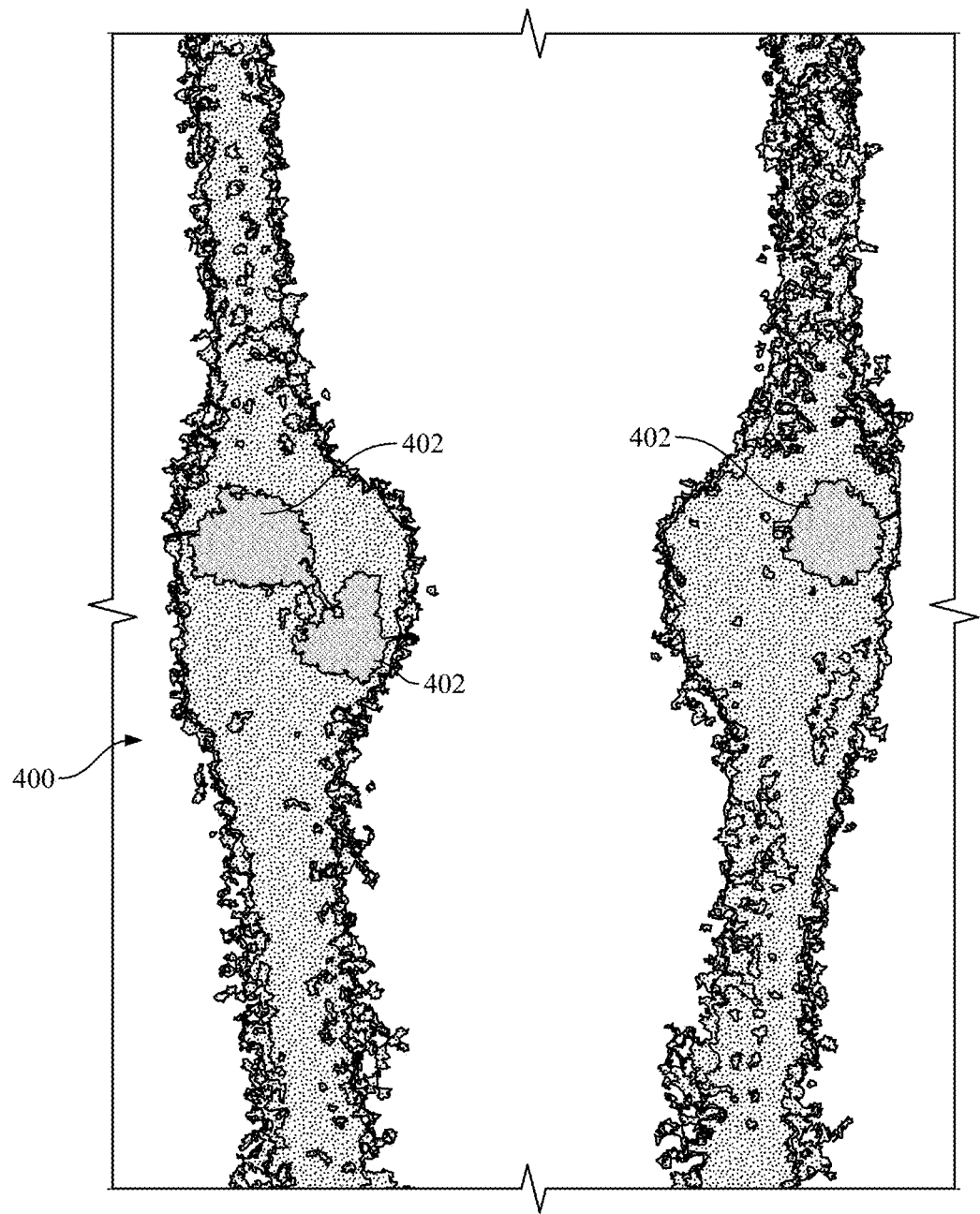

FIGS. 6A and 6B are illustrations of an exemplary image 400 created, displayed, and/or utilized by system 100. In the exemplary image 400, a bone scan created with the use of a gamma camera is shown with multiple hot spots 402, indicative of the location of the radiopharmaceutical. In some embodiments, a (e.g. surgeon, physician's assistant, nurse) creates a cut within tissue (e.g. bone) that would promote osteoblast formation and hot spot formation as the osteoblast will absorb the tracer. In such an embodiment, the tracer can be injected and/or placed directly on the cut such that the tracer remains substantially in place and avoids systemic introduction of the tracer. In an embodiment, different tracers may be absorbed into different tissues such as thyroid, liver, kidney, and the like. The system 100 is also capable of creating, displaying, and/or utilizing three-dimensional images using ultrasound, radialized isometry, and/or three-dimensional views anterior, posterior, and circumferential.

Figure 7:
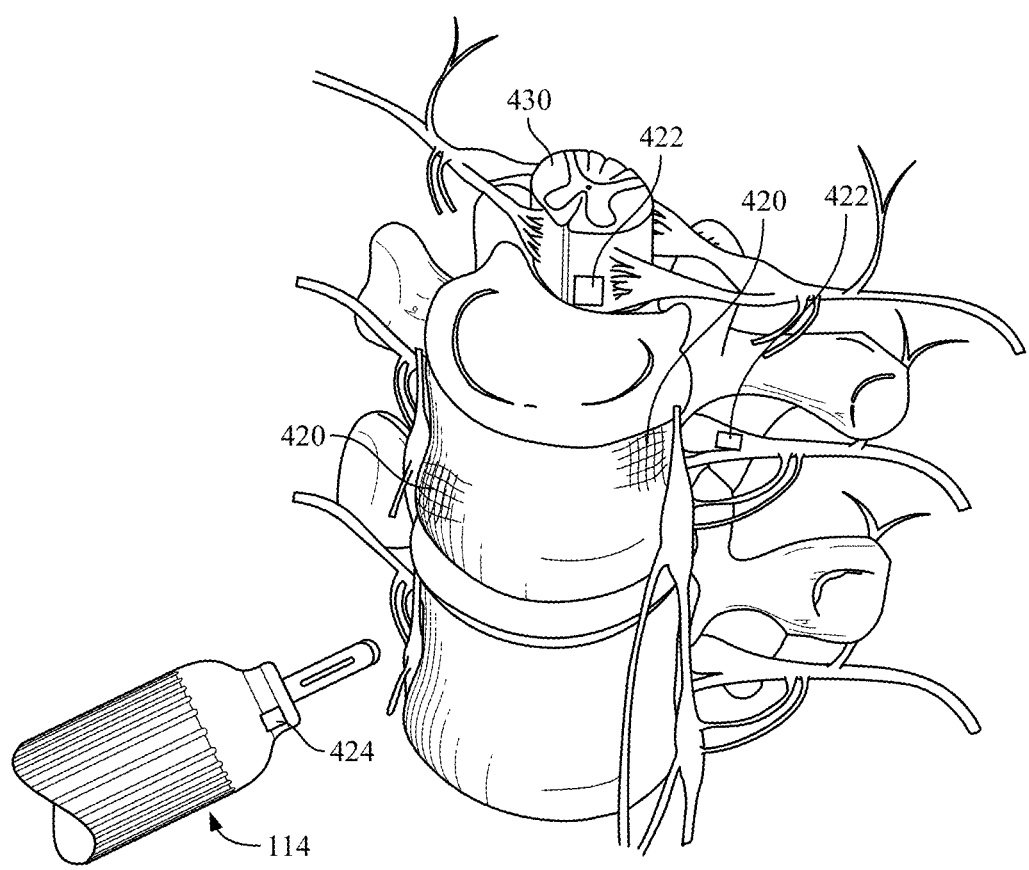
FIG. 7 is a perspective view of a portion of a spine having markers that may be sued with the system shown in FIG. 1.

In one embodiment, as shown in FIG. 7, in addition to, and/or in substitution of, creating tissue cuts, a user places one or more tissue markers 420 in discrete locations within the body. The tissue marker 420 can be injected, filled, or formed with a tracer to provide location information (e.g., via a thermogram). In one embodiment, the marker 420 is a scaffold that is formed to adhere to the contours of body tissue. The scaffold 420 may be formed to adhere directly to the tissue and/or be affixed with a fixation substance (e.g. surgical adhesive, bioadhesive, glue, fasteners, ultrasonic welding, other tissue reconstruction repair approaches). Alternatively, tracers can be compounded with an agent (e.g. PLLA, collagen) and positioned on the tissue with or without the use of a fixation substance. It should be noted that the markers can be biodegradable such that the tissue marker can remain in the body after the surgical procedure. Additionally, the markers can be fabricated from a non-biodegradable material. In some embodiments, the markers include a wireless transmitter (e.g. RFID tag, Bluetooth) that provides, at minimum, location information for inventory and/or complication risk assessment. Additionally, the markers can be sensors in the tissue.

In one embodiment, sensors 422 are positioned within a procedure site. The sensors 422 are configured to detect and transmit non line of sight surgical data to the surgeon, through system 100. Although the sensors are configured to communicate with system 100 in a wireless fashion, the sensors 422 can electrically couple to system 100 to communicate directly over a transmission line (e.g. fiber or metallic cable). In one embodiment, the sensors 422 would act as Geiger counters and detect tracers within a particular location. In an embodiment, sensors 422 are powered by capacitors. In another embodiment, sensors 422 are powered by body flow across cell membranes (i.e., turning tissue into a battery) by utilizing electrical energy through the membranes through thermal application. It should be noted that the body flow could be accomplished through synthetic tissue. In an embodiment, sensors 422 measure microcellular microcellular electrical gradients inside the cell. In some embodiments, sensors 422 are configured to detect force to provide feedback as to the forces exerted on and around tissue. In some embodiments, sensors 422 measure electrical pulses emitted by the body (e.g. nerves) during surgery. In such embodiments, sensors 422 can detect pulses by EEG, EMG, micro electrode arrays, or other electrophysiological recording methods. In one embodiment, sensors 422 are provided such that somatosensory evoked potentials are detected during a procedure. It should be noted that sensors 422 can be any sensor that monitors environmental factors including, but not limited to, force, acoustic, vibratory, density, pressure, optical, chemical, and electric. In some embodiments, sensors 422 are optical and/or biodegradable. Sensors 422 may also be positioned on the skin of a patient or implantable in the body of the patient. In some embodiments, sensors 422 partially degrade. For example, sensors 422 could include a biodegradable coating or slowly degrade over a specific time when exposed to water. The degradation may be hastened by heat, pH, and the like. In some embodiments, sensors 422 are rechargeable, such as through electromagnetic, optical, laser, ultrasound, vibratory, and/or thermal techniques.

In one embodiment, sensors 422 are configured to measure distances of particular tools. For example, as shown in FIG. 7, an end effector 114 (e.g. ultrasonic scalpel) may have an emitter 424 positioned at a fixed location. As end effector 114 is inserted in the body, system 100 can monitor the distance of the tool relative to sensor 422. In the exemplary embodiment, the sensor is placed on at least a portion of the spinal cord 430. As the tool would progress internally towards the spinal cord 430, system 100 and/or processor 122 would lock-out (prevent) end effector from functioning and/or progressing to prevent disruption of spinal cord 430. In some embodiments, sensors detect tools directly without the need for an emitter. For example, sensor may detect the vibratory or acoustic energy emitted by tool to determine a location of the tool relative to the sensor.

As noted above, system 100 can be calibrated such that the markers 420 and/or sensors 422 provide boundaries such that disturbances to portions of the body not part of the surgical procedure are minimized. Additionally, the markers 420 and/or sensors 422 can provide a secondary layer of protection should a fault occur. In such an embodiment, the markers and/or sensors can require the software of system 100 to perform a first check of calibration and confirm navigation throughout the procedure.

It should be noted that while methods and systems shown herein are depicted for arthroplasty, the methods and systems described herein can be utilized in any part of the body for any surgical procedure. For example, a tracer could be absorbed into organ (e.g. heart, gallbladder, etc.) which enables system 100 to create a boundary for procedural component 112 and/or end effector 114, such that the end effector does not work outside of the boundaries created using information obtained from markers 420, sensors 422, and/or scanners 302. Accordingly, as the soft tissue moves or is moved, system 100 can maintain an accurate location of the surgical site. Moreover, the methods and systems described herein can be utilized for robotics and/or haptics guided with preoperative imaging via CT, MRI, ultrasound techniques, and the like. The method and systems described herein may also be utilized standalone intraoperatively.

In the exemplary embodiment, system 100 receives instructions from software that enables processor 122 to determine boundaries within a surgical site and prevent (e.g., lock-out or disable) components 112 and/or end effectors 114 from operating outside of the determined boundaries. To this, if a components 112 and/or end effectors 114 are prevented from continued operation due to a boundary, system 100 and/or processor 122 is configured to determine whether to move the component 112 and/or end effector 114 or a portion (or all) of table 220 to enable further operation of the component 112 and/or end effector 114. In one embodiment, the determination of what object to move is provided to a surgeon to enable manual intervention.

Alternatively, system 100 provides signals to the appropriate object (e.g., effector 114 or table 220) to enable the procedure to continue. The signals provided to the table 220 can be any signals that effect a table to re-position a patient as needed, including but not limited to, manipulating, rotating, torqueing, twisting, distracting, flexing, extending, elevating, descending, inflating or utilizing a retractor (i.e., internal or external) or bolster that aid in bringing objects into/out of a surgical site. Such a repositioning of objects enables a surgeon to optimize portions of a body relative to a portal or incision. For example, system 100 is configured to provide instructions to manipulate vessel blood flow, organ position, or the position of any other body part. The signals provided to the table 220 can also be any signals that affect a table to move relative to a body part. The body part could also move relative to the table 220 and/or relative to other systems (e.g., 120, 122, 124, and 220) coupled to system 100. Moreover, the table and the body part could both move together synchronously or independently. In addition to providing instructions to manipulate table 220, system 100 can also provide instructions to other systems (e.g., 120, 122, 124, and 220) coupled to system 100. For example, system 100 manipulates a change in table 220, system 100 would also transmit a signal to adjust lighting or visualization to re-position to the new location of the surgical site. The signals described herein may enable control and/or activation of aspects of system 100 through voice commands, remote commands, imaging controls, and/or robotic activation. Aspects of system 100 may also be controlled with a robotic mechanism with or without navigation or visualization.

Additionally, if processor 122 determined that a repertory change of the patient would aid in the effectiveness of the procedure, a signal can be generated and transmitted to the anesthesia system and/or anesthetist to alter the anesthetic (e.g., amount or type) given. In an embodiment, processor 122 generates and transmits a signal to dictate anesthesia to, for example, increase or decrease inflation of the lungs, change the blood pressure, heart beat rate, lung volume, and the like. Moreover, processor 122 is capable of controlling electrical currents for transcutaneous electrical nerve stimulation (TENS) to stimulate muscular activity and/or vascular activity and control position. For example, electrothermal vibrations could be used to stimulate tissue and/or electrical soma.

Figure 8:
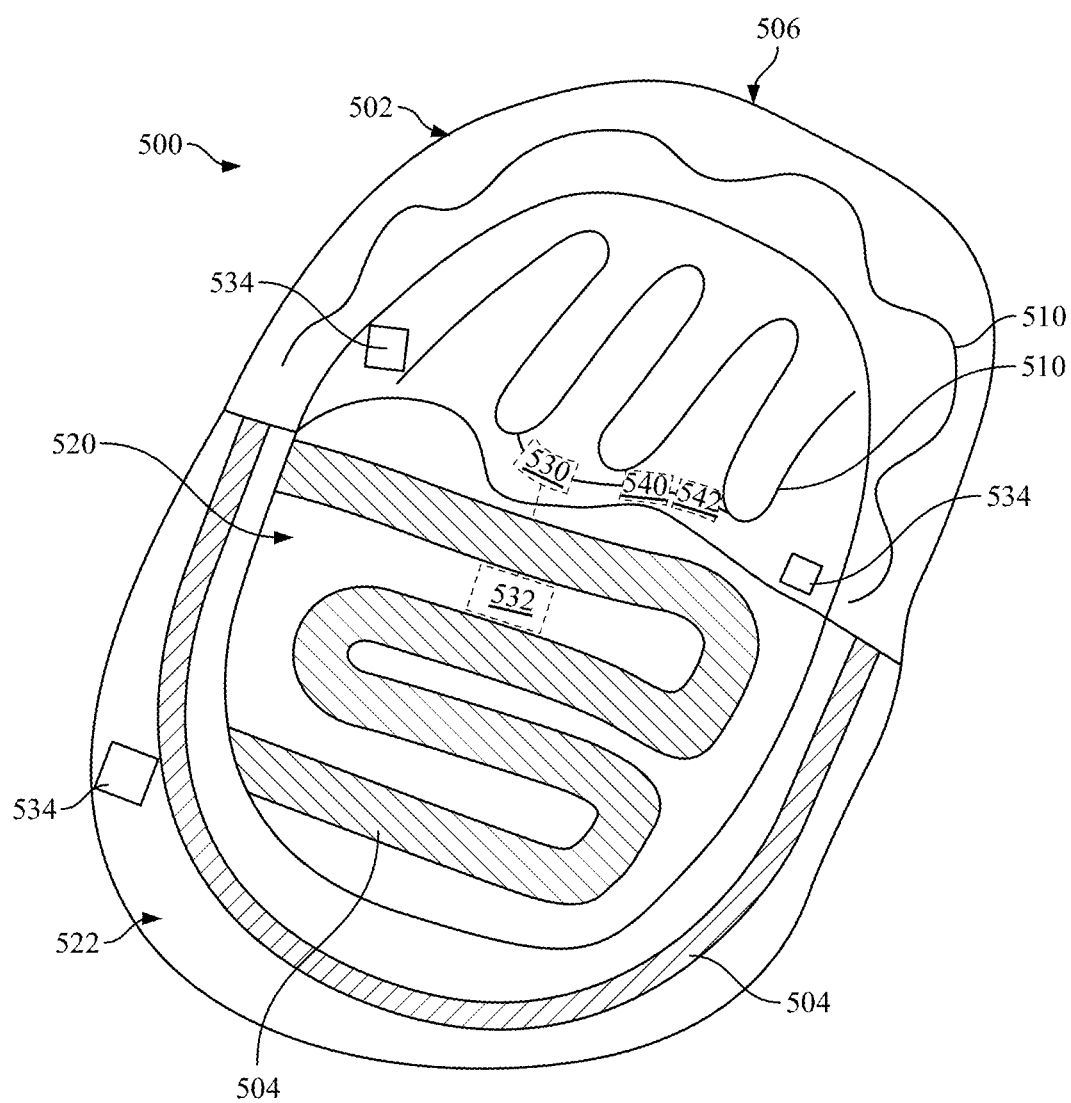
FIG. 8 is a cut-away perspective view of an exemplary temperature implant for use with the system shown in FIG. 1.

FIG. 8 is a cut-away perspective view of an exemplary temperature implant 500 for use with system 100 shown in FIG. 1. Implant 500 includes a heating portion 502 that provides heating to tissue in direct contact with implant 500. Implant 500 also includes a cooling portion 504 that surrounds and is adjacent heating portion 502 that prevents heating of tissue that is not in direct contact with heating portion 502. Heating portion includes a surface 506 that is configured to increase temperature as a result of a heating element 510 positioned within implant 500. Heating element 510 can be any element that produces heat to surface 506 including, but not limited to, metal, ceramic, and composite. In one embodiment, heat is produced from the use of vibratory (e.g. ultrasonic) energy. In the exemplary embodiment, surface 506 is fabricated to include a polymer but can include any material that enables heat transfer including, but not limited to, metals and polymer composites. In some embodiments, heating portion 502 includes a magnetic surface. Heating element 510 can also be any element that produces electrical charges to an implant surface, cell membrane, tumor, or infection, for example through microscopic membranes, cell membranes, nerve fibers, mitochondria, and/or intracellular.

To provide cooling to implant 500, cooling portion 504 includes a heat exchanger to reduce heating of tissue that is not in direct contact with surface 506. In one embodiment, implant 500 is fabricated to be modular. In such an embodiment, implant 500 is fabricated to have multiple removable sections such as a base section 520 and first modular section 522. Modular section(s) 522 can be added or removed to increase or reduce the size of the implant 500 thus providing for a variable sized implant.

In the exemplary embodiment, heating element 510 and/or cooling portion 504 is powered by a controller 530 and power source 532. In one embodiment, power source 532 is a battery. Alternatively, power source 532 is a power converter that converts power (e.g. A/C or D/C current) from a power source (e.g. outlet) into electrical signals for use by the heating element 510 and/or heat exchanger 504. Implant 500 also includes sensors 534 configured to monitor environmental factors within the operating site. In one embodiment, a sensor 534 is temperature sensor configured to monitor the temperature of implant 500 and/or the tissue in contact with surface 506 and/or the tissue adjacent to implant 500. Additionally, the sensors 534 can be any sensor that monitors environmental factors including, but not limited to, force, acoustic, vibratory, density, pressure, optical, chemical, and electric. In some embodiments, implant 500 includes a timer (not shown) coupled to controller 530 that enables controller to selectively provide power to heating element 510 at predetermined times or intervals. In an embodiment, sensors 534 are internal sensors.

Sensors 534 are coupled to a communication interface 540 coupled to processor 542 and/or controller 530. Communication interface 540 communicates with system 100, shown in FIG. 1. In addition to providing operating site information, communication interface 540 also receives instructions, remotely, for powering and adjusting parameters (e.g. temperature) of implant 500. To communicate with system 100, communication interface 540 may include, for example, a wired network adapter, a wireless network adapter, and/or a mobile telecommunications adapter. Moreover, communication interface 540 may communicate via nerve transport, cellular membrane transport, and/or cellular signals.

In use, implant 500 is placed on tissue. In some embodiments, implant 500 heats tissue for a predetermined amount of time and then removed. After removal, a thermogram scan can be taken to provide landmark information to system 100. In one embodiment, implant 500 remains positioned within the body to allow for selective heating of tissue throughout the procedure. The resulting thermogram images can be co-registered with other images (e.g. CT, MRI, X-Ray, Gamma) taken of the patient to provide landmark information to system 100 and/or the surgeon. In some embodiments, the thermogram can be utilized as an alternative to the radioisotopes described above. The advantages of the use of implant 500 and the resulting thermogram images is that landmark information can be provided and registered without having direct line of site enabling the implant 500 to be positioned on the side, back, or into the padding behind the arthroplasty as one would not require direct line of site, which would impede the surgical procedure. In some embodiments, implant 500 uses electrical, thermal, and/or magnetic techniques to stimulate muscle, vessels, nerves, and the like to contract over movement patterns. Landmark information can be detected by creating boundary levels as well as navigation. For example, a stimulator would move to detect where the movement is and then create boundary layers or guidance direction to a specific site.

In one embodiment, system 100 includes a scanner 302 in the form of a vessel determination device. The scanner is configured to locate vessels and flow rates in the body. The scanner 302 can include any flow determination technology for locating vessels including, but not limited to ultrasonic flow meters and/or laser Doppler velocimeters. Once the vessels are located, positional information can be transmitted to system 100 to be input into images and navigation calibration. In one embodiment, system 100 determines the type of vessel (e.g. artery, vein, capillary) based on the size and/or flow rates of the located vessels. Vessels that are within a procedure site can be used as boundaries such that procedural component 112 and/or end effector 114 will be disabled when approaching the vessel to maintain patient safety during the procedure.

Figure 9A:
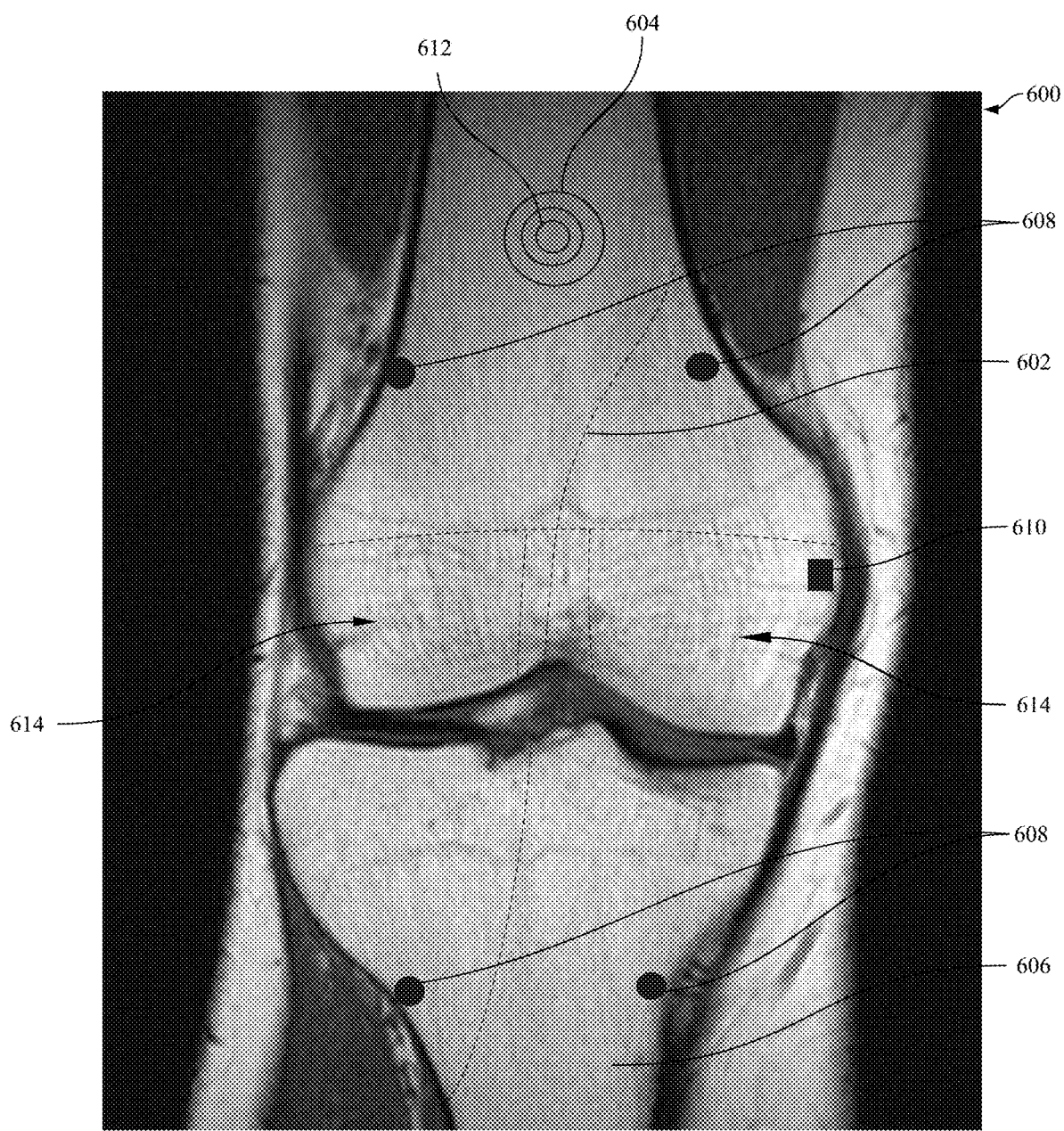
FIG. 9A is an exemplary image produced by the system shown in FIG. 1.
Figure 9B:
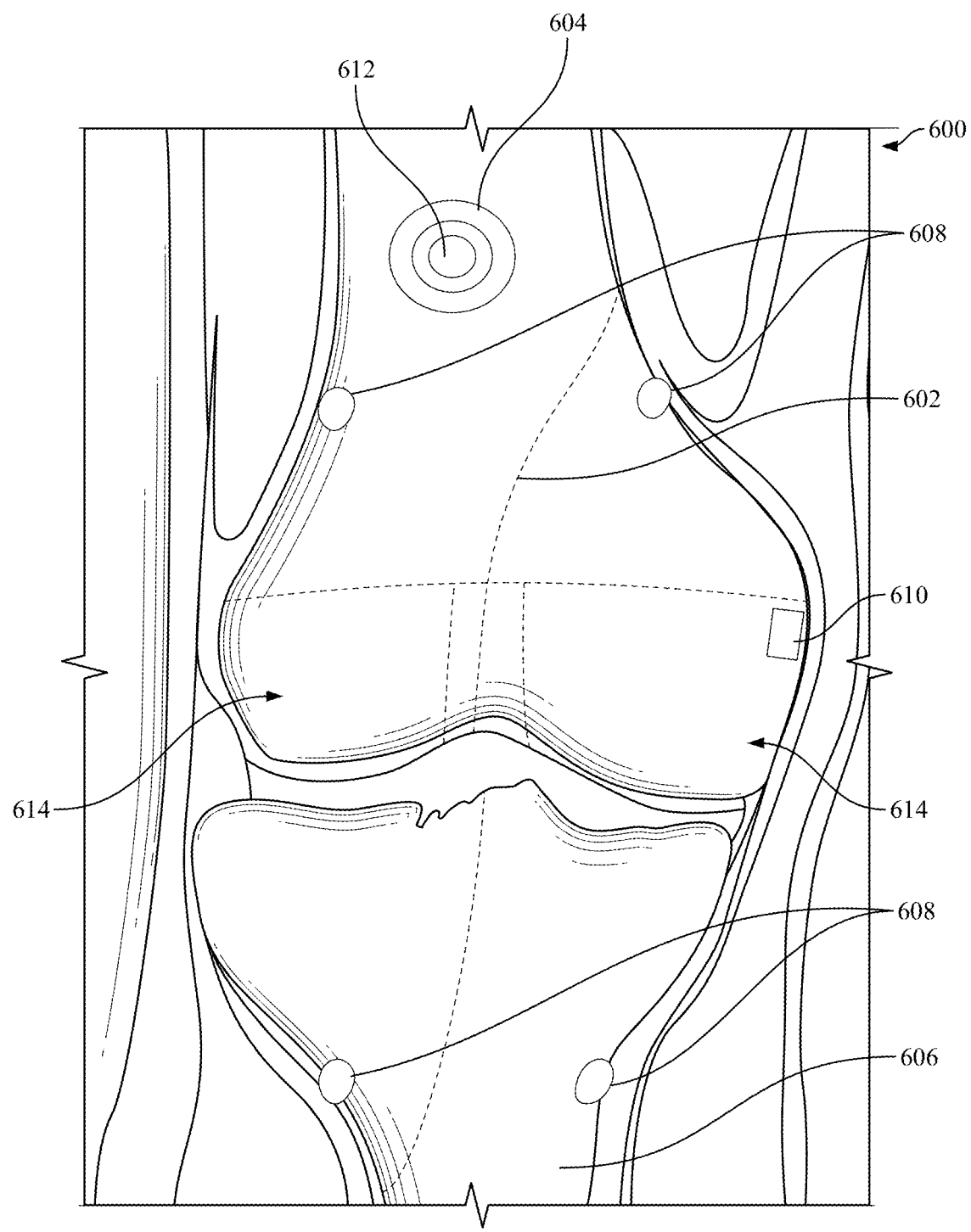
FIG. 9B is a schematic of the exemplary image shown in FIG. 9A.

FIG. 9A is an exemplary image 600 created by processor 122, shown in FIG. 1, using information received from scanners 302 for display on interface 106. FIG. 9B is a schematic representation of image 600. Image 600 is created by co-registering multiple images created from scanners 302. As can be seen in the image, a knee joint having a femur 604 and tibia 606 are created from an MRI. Image 600 also displays a vessel 602 positioned behind the femur 604 and tibia 606 from flow determination technology. Radioactive tracer information is shown by hot spots 608 that were derived from a gamma camera or PET, ands sensors 422 or markers 610 can be located as well. Image 600 also includes thermography information 612 from the patient. In one embodiment, image 600 includes cutting guides 614 that display portions of tissue that will be removed by the surgeon. It should be noted that any and all of the landmarks, sensors, or makers that can be identified by system 100 can serve as boundaries or limitations on procedural components 112 and/or end effectors 114. Additionally, any of the imaging and/or landmark determination techniques described herein can be combined such that processor 122 can co-register the information to produce images and instructions for system 100.

In addition to image 600, processor and/or system 100 can also generate a composite image of the surgical site in the form of an animation or 3-D rendering based on the information shown in FIG. 9. Such an image would provide a reconstruction of the surgical site enabling the surgeon to rotate through the surgical site and visualize the entire site from any desired angle. As noted above, the images produced would also enable a surgeon to receive a holistic view of a site. For example, while a portion of image 600 displays a portion of the knee, a surgeons' view would provide views of the pelvis, hip, foot, and ankle for relative information. Such information is vital to determine how objects in the surgical site (e.g., knee movement) affect remote portions of the body (e.g., hip, spine, and ankle). In addition to optical changes, the images produced may also enable detection of electrical and/or motion patterns.

In the exemplary embodiment, the images produced by system 100 also provide a surgeon the ability to locate anatomical structures (e.g., bones, organs, arteries, vessels, cartilage) in a surgical site and denote those structures by color coding or labeling. Such structures can also be removed or added to a view, via input interface 104, during a procedure based on the surgeons' needs. Images produced by system 100 may also be utilized for external ablation systems that utilize ultrasound, thermal, and like techniques to refine exact tissue location for ablation of tumors, treatment of infection with antibiotics to enhance growth, neurologic tissue, rewire neurons, and/or repair complex neurological bundles.

To decrease the trauma (e.g. pain, swelling, etc.) received or resulting from a surgical procedure, surgical markers and/or sensors can be positioned at points of interest for a surgeon. The surgical markers are substances including a dye that fluoresce when exposed to ultraviolet light (UV). As an alternative to directly placing the surgical markers on tissue, tissue closure devices (e.g. suture, staples) can be impregnated with the dye such that it is absorbed or transferred to the tissue that is in direct contact with the closure device. For example, in a revision arthroplasty procedure in which an infected joint replacement component is being extracted and replaced, the surgeon can position surgical markers on the incision or open tissue after he/she extracts the joint replacement component and before closing the surgical site to allow the body to eliminate/fight the present infection. When patient returns for the secondary procedure (e.g., placing a drug local into the body), ultraviolet light can be used to locate former incision locations. Using the UV indicated locations, a surgeon can utilize the former incision to open the surgical site. Utilizing a former incision can greatly reduce pain, inflammation, and trauma to the patient as scar tissue generally forms at locations of former incisions, which has been found to be less traumatic to a patient than disturbances (i.e. cuts) to muscle tissue.

In addition to the images created in system 100 from imaging devices 110, system 100 can include software filter for filtering out material and/or objects from an image that can restrict line of sight of a user (e.g., physician/surgeon, driver, machine operator, etc.). For example, the filters described herein would enhance the surgeon's ability to visualize a surgical site during a procedure (e.g., arthroscopy) by filtering opaque bleeds or blood flow and allowing the surgeon to determine the location or source of the bleed. In another exemplary embodiment, the filters described herein would enhance the driver's ability to visualize upcoming stretches of roadway by filtering fog, rain, and the like and allowing the driver to determine if hazards exist on the upcoming stretches of roadway. When video is digitized, each frame is represented by a two dimensional array. Each location in the array represents a pixel and each pixel contains a set of values representing color and other attributes. The filters described herein manipulate these pixel values. For example, the filters described herein may change pixels and/or remove pixels with or without electrical charges or motion changes. It should be noted that these filters could be applied to any video format and coding methods including, but not limited to, PAL, NTSC, MP4, and AVI.

In one embodiment, a first filter is utilized within system 100 and the first filter is configured to determine when blood exists in the saline solution of a surgical site during surgery. This is accomplished by monitoring a sequence of frames for a range of target colors that move in a particular pattern. In one embodiment, the first filter lowers the color values of blood to match the surrounding colors. Alternatively, the first filter lowers the intensity of color of blood (e.g. red) to enable the surgeon to better visualize the intended area. In some embodiments, the first filter lowers the color values and well as lowering the intensity of color. For example, one could see the reflective coefficient (e.g., albedo), albedo with different light sources, and/or different movement creating the changes. In some embodiments, the first filter accomplishes the determination with vibratory changes, acoustic changes, moving cells that change, and/or move or have specific electrical charges. The first filter could remove these pixels in the tissue/bone. In some embodiments, the target (e.g., tissue) may be magnetized. In some embodiments, the filter bounces, changes, and/or reflects light. For example, the filter could enable a user to see around corners with reflective light by using an albedo or reflective coefficient.

In another embodiment, a second filter is utilized by system 100 to provide images to a user. The second filter is configured to adjust particular colors in an image by removing pixels in each frame that meet a predetermined criteria (e.g., blood flow). The pixels in the buffer which would be displayed on a standard image without the use of second filter would then be used in place of the obscured pixels. This would give the second filter hysteresis which would allow it to use previous information to help recreate what is behind an object (e.g., blood, synovium, tissue fats, debris, bone fragments) that could obscure the view other objects of interest (e.g., soft tissue, cartilage, muscle, bone). It should be noted that the first and second filters could be used in combination to provide an accurate rendering of a surgical site enabling a surgeon to selectively eliminate unnecessary objects from their view. For example, multiple filters could be used to change orange pixels to red pixels. In some embodiments, one filter is a software filter, for example a mechanical filter (e.g., film, prism, Fresnel lens, UV lens).

In some embodiments, the second filter is utilized by generating a baseline image and comparing the baseline image to new images taken at predetermined time increments (e.g., 0.1, 0.5, 1, 2, 30 seconds or minutes). In such embodiments, pixels could be compared to determine flow patterns of fluid or other moving objects. Additionally, system 100 is configured to enhance objects in an image by receiving imaging information, comparing to known imaging information (e.g., pre-operative scan), determining the differential and adding necessary data to the received imaging information.

FIG. 9 is an exemplary flowchart 700 of a method of visualization for use with the system 100 shown in FIG. 1. In the exemplary embodiment, system 100 receives an image of a site. In some embodiments, an image _____ is received by computing device 102 from an imaging device 110 and or input interface 104. In some embodiments, images _____ are received by computing device 102 from a remote location through communications interface 108.

FIGS. 10-13 are images utilized with the method shown in FIG. 9.

In some embodiments, system 100 utilizes filters to determine the source of the blood flow. Once system 100 and/or processor 122 determines the location or source of a blood flow, system 100 can indicate, on the image, the source of the blood. Additionally, system 100 can also indicate a particular concentration of blood in the image at certain areas where the blood is has stronger concentration. In some embodiments, system 100 can determine the velocity of the blood flow in one or more locations, which may indicate the source of blood flow. Any of the determinations described above, can be indicated on an image, by system 100 and/or processor 122, with indicia having non-limiting examples of a circle, marker, or color differentiation so that the surgeon can easily locate the area of blood flow to allow for electrocautery, to locate the source of the bleed, and/or to apply pressure for coagulation.

In one embodiment, a diagnostic ultrasound or B-Mode ultrasound head is imbedded into an imaging device 110 (e.g., camera) to enable overlaying the information from the diagnostic ultrasound with the video image in real time. This provides the surgeon a 3-dimensional view of the surgical site as well as the direct camera view. Such a combination is useful in removing blood or other debris from the surgeon's view with filters. In some embodiments, a second portal or external ultrasound is utilized in conjunction with the camera to enable these filters as well. If either internal or external ultrasound is used, it is possible to use Doppler information to better detect blood for filtering. The filters would work as previously mentioned for either removal the color or using information from previous frames. The Doppler information is useful in a more precise determination of the location of the bleed. The filter should also monitor for dramatic increase in the blood flow. If system 100 determines an increase in blood flow has occurred, an alert is transmitted to the users that a bleed is occurring and being filtered out that might require attention. In one embodiment, the alert is provided as an overlay warning the surgeon of the increase in blood flow. Alternatively, system 100 can be configured to turn off filters when an amount of blood in the field of view exceeds a predetermined threshold. In some embodiments, system 100 is configured to filter out objects that produce a reflection at or above a predetermined threshold.

In one embodiment, system 100 creates a charged particle filter used for filtering out particular objects. In such an embodiment, system 100 projects or transmits a number of charged particles (e.g., ions in a gas) at a site that attach to a particular object. The charge is selected by determining an object to be filtered out and charging particles to a predetermined setting that would enable the particles to attach or couple to the object. Once the particles attach to the object, system 100 detects the location of the objects and filters out the information from the images generated.

In some embodiments, physical optical filters are utilized on or with lighting and visualization systems to aid in visualization. For example, physical filters could be applied to the lights to substantially block a predetermined color (e.g., red) from appearing in the imaging. Alternatively, physical filters can be utilized to substantially increase the brightness or coloration of particular color in an image. As such, the physical filters can be applied to block out additional unwanted properties (e.g., UV, sun photons).

In the exemplary embodiment, system 100 is configured to enable a surgeon and/or user to switch between the filters, combine particular filters, remove particular filters, and turn the filters on and off all together. While the software filters discussed above were provided in the application of blood during surgery, these techniques could also be used to eliminate other unwanted elements of an image including, but not limited to, smoke that is released during electrocautery, or moving objects and debris in the view of the camera. The visualization system described herein is valuable because the system 100 enables a surgeon to operate or perform a surgical procedure in a substantially dark room reducing heat from the lights, which can be detrimental during a procedure and affect tissue healing. Additionally, the system described herein eliminates the necessity for water or carbon dioxide air during an endoscopic procedure.

In some embodiments, imaging device 110 is an ingestible-type camera for examination of the internal system of a body (e.g. abdomen). An endoscopic application, colonoscopy, or microsurgery could be used to repair individual nerve fibers or vascular fibers. Aspects of system 100 could be used for cardia ablation to localize exactly where irregular cardiac rhythms are coming from.

Figure 10:
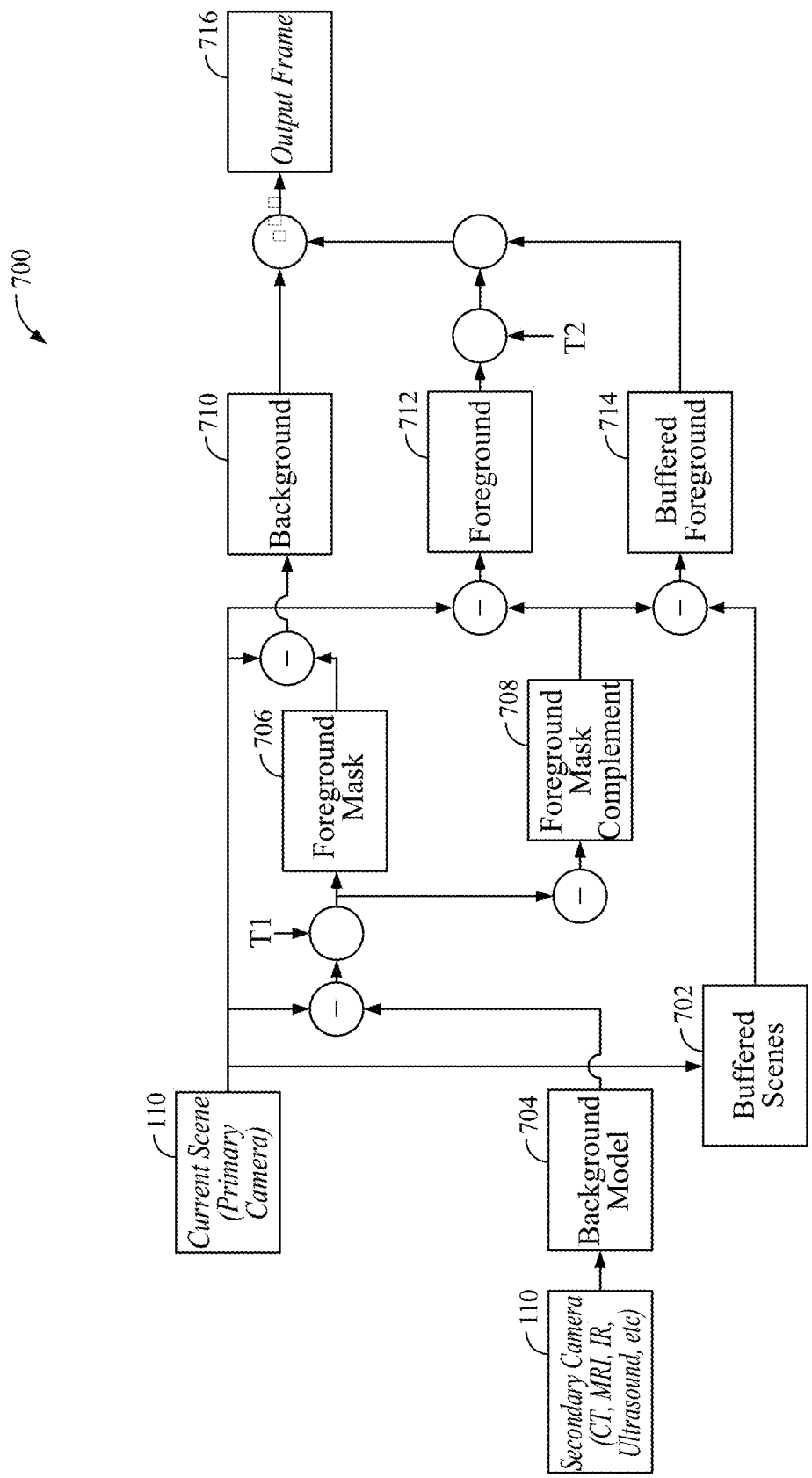
FIGS. 10-12 are exemplary data flow diagrams of filtering images performed by the system shown in FIG. 1.

FIG. 10 is a data flow diagram of an exemplary two-input filtering method 700 for use with the system 100 shown in FIG. 1. In the method 700, computing device 102 creates buffered scenes 702 from current scenes captured by a primary camera (e.g., imaging devices 110). The computing device 102 uses scenes captured by a secondary camera (e.g., imaging devices 110) to create a background model 704. The secondary camera may capture images using CT, MRI, infrared, ultrasound, and/or like techniques. The computing device 102 subtracts the background model 704 from the current scene captured by the primary camera utilizing a threshold (T1) to create a foreground mask 706. Moreover, the computing device 102 takes the complement of the foreground mask to generate a foreground mask complement 708 (i.e., a background mask). The computing device 102 subtracts the foreground mask 706 from the current scene captured by the primary camera to generate a background 710. The computing device 102 also generates a foreground 712 by subtracting the foreground mask complement 708 from the current scene captured by the primary camera. And the computing device 102 subtracts the foreground mask complement 708 from one or more buffered scenes 702 to generate a buffered background 714. The computing device 102 generates a weighted average or threshold (T2) of the foreground 712 and the buffered background 714. The computing device 102 then generates an output frame 716 by determining the absolute difference between the background 710 and the weighted average.

Figure 11:
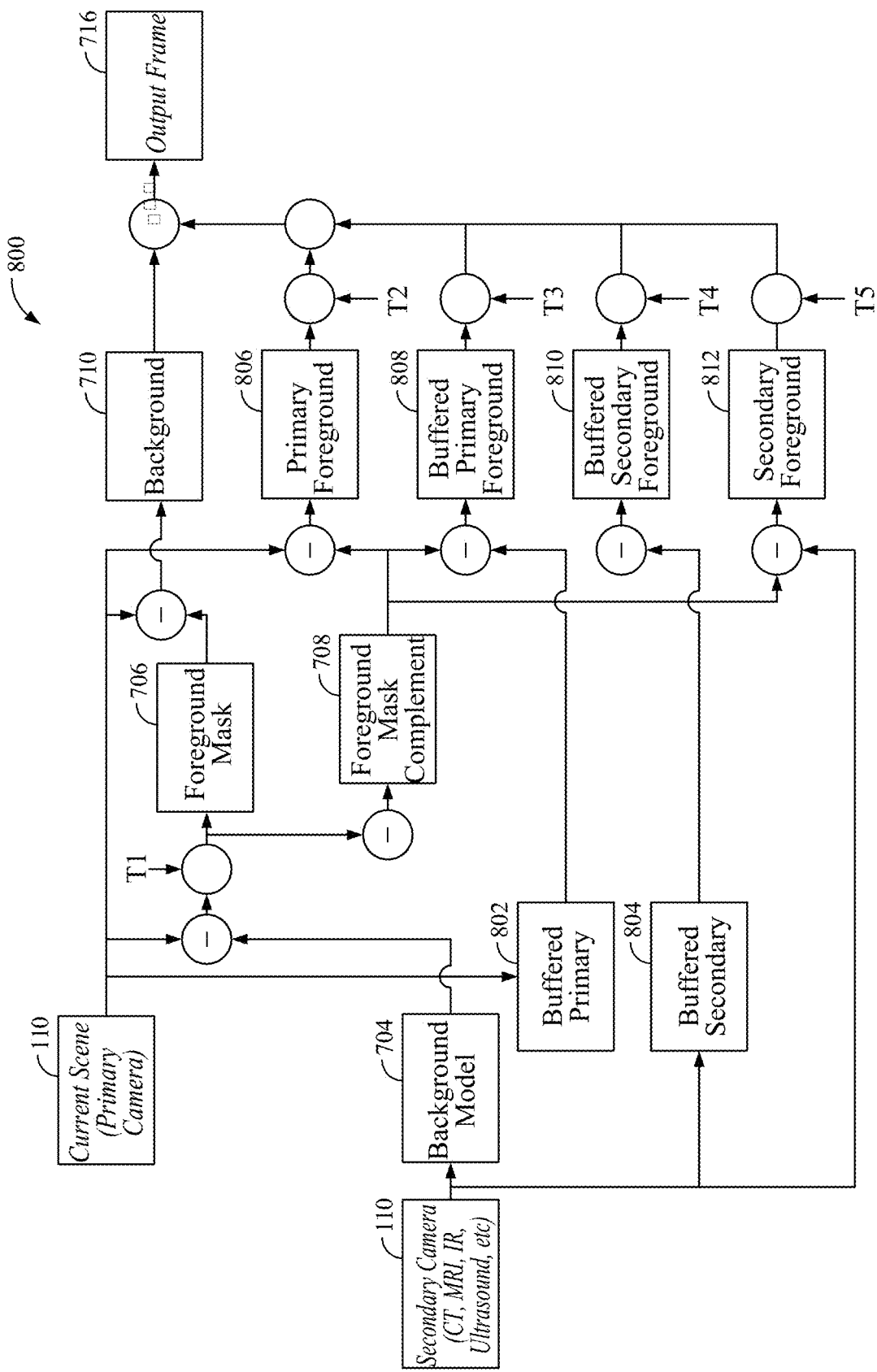

FIG. 11 is a data flow diagram of an exemplary two-input filtering method 800 for use with system 100 shown in FIG. 1. In the method 800, the computing device 102 creates buffered primary scenes 802 from current scenes captured by the primary camera and buffered secondary scenes 804 from current scenes captured by the secondary camera. The computing device 102 uses the buffered primary scenes 802 and buffered secondary scenes 804 to find frames where the object in the foreground obstructing the view is not present. In this embodiment, the computing device 102 may create the background model 704 from any combination of the primary input, secondary input, output frame 716, primary buffer 802, and secondary buffer 804. As described above, the computing device 102 utilizes the background model 704 to create a foreground mask 706 from the primary camera. In addition to generating the background 710 as described above, the computing device 102 applies the background mask 708 to the primary camera input to generate a primary foreground image 806. The computing device 102 also applies the background mask 708 to the secondary camera input to generate a secondary foreground image 812. To create a buffered primary foreground image 808, the computing device 102 applies the background mask 708 to images selected from the buffered primary scenes 802. And the computing device 102 generates a buffered secondary foreground image 810 by applying the background mask 708 to images selected from the buffered secondary scenes 804. The computing device 102 takes a weighted average of the primary foreground image 806 over time T2, the buffered primary foreground image over time T3, the buffered secondary foreground image over time T4, and the secondary foreground image 812 over time T5. The final output frame 716 is generated by the computing device 102 taking the absolute difference between the weighted average and the background image 710.

Figure 12:
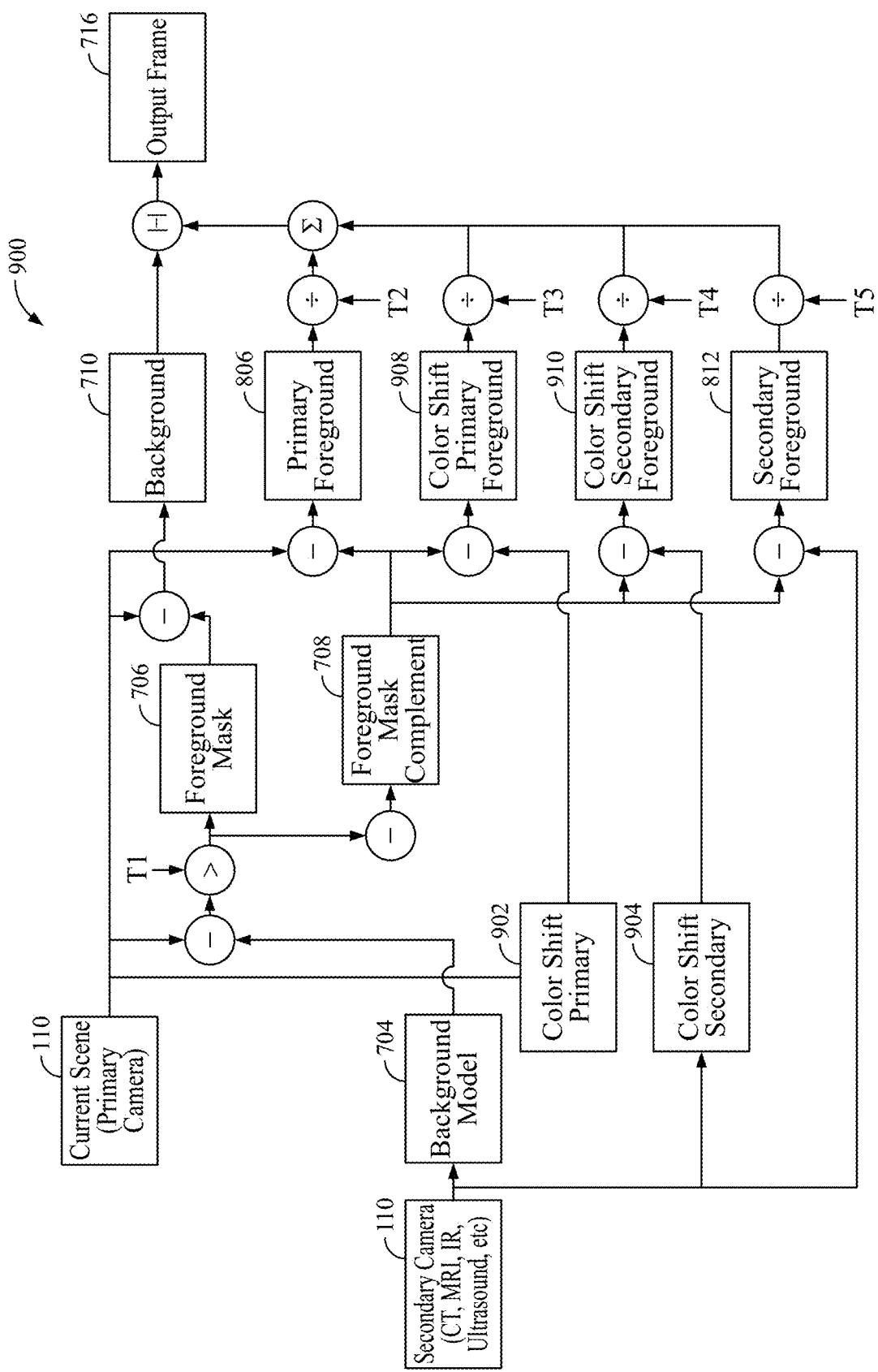

FIG. 12 is a data flow diagram of an exemplary color shift filtering method 900 for use with system 100 shown in FIG. 1. In the method 900, the computing device 102 creates a primary color shift image 902 from the primary camera input and a secondary color shift image 904 from the secondary camera input. In an embodiment, the color shifts are dependent upon one or more wavelengths of interest. The computing device 102 applies the background mask 708 to the color shifted primary image 902 to create a color shift primary foreground image 908 and applies the background mask 708 to the color shifted secondary image 904 to create a color shift secondary foreground image 910. The computing device takes a weighted average (T2) of the primary foreground image 806, the color shift primary foreground image 908 threshold (T3), the color shift secondary foreground image 910 threshold (T4), and the secondary foreground threshold (T5). The final output frame 716 is generated by the computing device 102 taking the absolute difference between the weighted average and the background image 710.

The system and methods described above could be used in tumor, oncology, endoscopic, arthroscopic, and/or tissue ablation procedures such as ultrasound ablation. For example, the system and methods could be used for guidance, direction, and/or location tasks during surgical procedures. In some embodiments the system and methods could be done on a macroscopic level and in some embodiments the system and methods could be done on a microscopic level, looking for specific cells, movement patterns, visualization patterns, and/or electromagnetic patterns. In an embodiment, the system and methods described above could be used to detect cells such as tumor cells or infections, which could be removed with navigation visualization provided by aspects of the system and methods. For example, one could have a patient adjust or intravenously give a marker that would absorb by abnormal cells such as a tumor or infectious cells and then visualization aspects of the system and methods could be utilized to remove pixels or enhance pixels with types of light frequency, vibrations, and the like. The tumor or infectious cells could be removed either by external tissue ablation such as ultrasonic, thermal guided ablation, or internally. Moreover, it could guide surgeons during removal of specific cells both on a macroscopic and microscopic level. For example, cells of amyloid deposits for Alzheimer's disease and/or cells that create hypertrophic tissue or infectious tissue.

While the system and methods described above have been described in a non-limiting medical setting, it should also be noted that the systems and methods described above (e.g., software filters) could also be used in non-medical applications, such as optimizing a heads up display on a car when there is fog or rain. In such an embodiment, a vehicle system can be configured to utilize the filters described above to filter objects (e.g., fog, mist, sun, pollution, smoke, or rain) and provide a clear image to vehicle passengers' either in place of a passengers' view or as an addition to a passengers' view. Such a system is also configured to detect objects in the path of the vehicle and alert passengers of the detected objects.

The embodiments described herein enable non line of sight structures and/or landmarks in the body to be observed before, during, and/or after a surgical procedure. As compared to at least some known navigational systems that require objects to be affixed to the body through invasive measures, the systems and methods described herein are capable of providing information to a robotic system to enable calibration and/or boundary layer configuration to assist in creating a more efficient and safe surgical procedure. The methods and systems described herein provide surgeons the ability to calibrate a robotic system and perform surgical procedures without direct line of site needed in known systems. The method and systems described herein could vibrate the visual fields as particles would have different vibratory frequencies based on their densities, thickness, or movement. The particles with variable movement patterns could then be removed. For example, this could be done through vibratory, acoustic, electromagnetic, external compression, internal compression, magnetic frequency, and the like. Although there may be a slight delay, any delay would not affect visualization for surgery treatment or non-surgical tasks.

The embodiments described herein may utilize executable instructions embodied in a non-transitory computer readable medium, including, without limitation, a storage device or a memory area of a computing device. Such instructions, when executed by one or more processors, cause the processor(s) to perform at least a portion of the methods described herein. As used herein, a "storage device" is a tangible article, such as a hard drive, a solid state memory device, and/or an optical disk that is operable to store data.

Although specific features of various embodiments of the invention may be shown in some drawings and not in others, this is for convenience only. In accordance with the principles of the invention, any feature of a drawing may be referenced and/or claimed in combination with any feature of any other drawing. Accordingly, while many procedures described herein relate to arthroplasty or orthopedic surgery, the methods and systems described herein can be utilized in any surgical procedure including, but not limited to, general surgery, cardiothoracic surgery, tissue ablation, ultrasound ablation, arthroscopic procedures, endoscopic procedures, cardiology and electrophysiology procedures, colon and rectal surgery, plastic surgery, anesthesia, pain management procedures, ENT procedures, gastrointestinal surgery, gynecology procedures, neurosurgery, oncology procedures, pediatric procedures, radiosurgery, reconstructive surgery, spine surgery, transplant surgery, urology procedures, and vascular surgery. Additionally, it should be noted that the systems and methods described herein could be utilized to provide encryption technology by determining known patterns and either accepting or rejecting based on a determination that known patterns have been detected.

While system 100 has been described as including a procedural component 112 and at least one end effector 114, it should be noted that system 100 can operate independently to provide visualization and/or navigation to users. For example, system 100 can be utilized in a manual surgical environment where system 100 provides surgical site information to a surgeon operating manually (i.e., without robotic assistance). Additionally, the system 100 described herein can be utilized to provide visualization and/or navigation with other non-medical and/or non-surgical applications. For example, portions of system 100 and method 700 can be installed in vehicles to provide the visualization and/or navigation needed. Portions of system 100 and method 700 can be utilized to enable a driver/passenger to "see through" objects that would limit sight. In the case of a car, truck, motorcycle, bus, or other land vehicle, system 100 and method 700 is utilized to remove fog, cloud cover, rain, sunlight, hail, mist, pollution, smoke, snow, or any other form of debris obfuscating in air or fluid media from a visual image to provide a substantially clear image of the path of travel of the vehicle. Consequently, the system 100 is configured to provide the same visualization to air vehicles (e.g., plane, spaceship, rocket, balloon, unmanned aerial vehicle (UAV) (e.g., drone)) and water vehicles (e.g., boats, ships, and submarines). Additionally, portions of system 100 and method 700 can be utilized in any application reproducing video or image feeds including, but not limited to including, residential and commercial surveillance systems, television production systems and equipment, telescopes, binoculars, marine applications, and satellite imagery. It should also be noted that the system and method described herein can be utilized with technologies described in U.S. patent application Ser. Nos. 14/451,562, 10/102,413, 13/559,352, and 62/275,436, each of which is hereby incorporated by reference in their entirety.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

A robotic system for navigation of a surgical site is provided. The robotic system includes a computing device coupled to a presentation interface, a procedural component, and a communications interface. The computing device is also coupled to a first imaging device configured to provide imaging data of a surgical site. The computing device is also coupled to a second computing device that is configured to provide a second type of imaging data of the surgical site that is different that the imaging data of the first imaging device. The computing device is configured to co-register the imaging data to create a surgical site image for display to a surgeon on the presentation interface.

What is claimed is:

1. A system for visualizing a surgical site, the system comprising:
   a robotic mechanism for performing a procedure on a patient;
   an imaging device coupled to the robotic mechanism, the imaging device configured to provide image data of a site of interest;
   a computing device coupled to the imaging device, the computing device including one or more processors and at least one memory device configured to store executable instructions, the executable instructions, when executed by the processor, configured to:
   receive the image data of the site of interest;
   differentiate between at least one object of interest and at least one detected obstruction;
   filter the received image data to remove the at least one detected obstruction and recreate pixels related to the at least one detected obstruction based on at least one of (i) one or more buffered frames and (ii) one or more pixels adjacent to the pixels related to the at least one detected obstruction;
   generate an output frame from the filtered image data; and a presentation interface device coupled to the computing device, the presentation interface device configured to present the output frame for visualization of the site of interest.

2. The system of claim 1, wherein pixels related to the at least one detected obstruction are recreated based on both (i) one or more buffered frames and (ii) one or more pixels adjacent to the at least one detected obstruction.

3. The system of claim 1, wherein the at least one detected obstruction is at least one of blood, synovium, tissue fats, debris, bone fragments, and smoke.

4. The system of claim 1, wherein pixels related to the at least one detected obstruction are recreated based on (i) one or more buffered frames.

5. The system of claim 4, wherein the one or more buffered frames comprise a baseline image.

6. The system of claim 5, wherein the computing system is configured to compare the received image data to the baseline image.

7. The system of claim 6, wherein the computing system is configured to determine based on the comparison of the received image data to the baseline image that the detected obstruction is obstructing the object of interest in the received image data.

8. The system of claim 5, wherein the computing system is configured to mask the received image data to superimpose pixels related to the object of interest based on the baseline image onto the received image data over the pixels related to the detected obstruction.

9. The system of claim 1, wherein pixels related to the at least one detected obstruction are recreated based on (ii) pixels surrounding the at least one detected obstruction.

10. The system of claim 1, wherein the computing device is configured to cease filtering when the at least one detected obstruction exceeds the predetermined size threshold.

11. The system of claim 1, wherein the computing device is configured to alert when the at least one detected obstruction exceeds the predetermined size threshold.

12. The system of claim 1, wherein the object of interest comprises a source of a bleed and the detected obstruction comprises an opaque blood flow.

13. The system of claim 1, wherein the detected obstruction comprises opaque blood.

14. The system of claim 13, wherein the computing device is configured to adjust a color value of the pixels related to the opaque blood based on a color value of one or more adjacent pixels.

15. The system of claim 13, wherein the computing device is configured to adjust an intensity of the pixels related to the opaque blood based on an intensity of one or more adjacent pixels.

16. The system of claim 1, wherein the computing device is configured to adjust a color value of the pixels related to the detected obstruction based on color values of one or more adjacent pixels.

17. The system of claim 1, wherein computing device is configured to adjust the intensity of the pixels related to the detected obstruction based on color values of one or more adjacent pixels.

* * * * *